US009536041B2

(12) United States Patent
Xiao et al.

(10) Patent No.: US 9,536,041 B2
(45) Date of Patent: *Jan. 3, 2017

(54) METHODS AND DEVICES FOR SINGLE-MOLECULE WHOLE GENOME ANALYSIS

(71) Applicant: BioNano Genomics, Inc., San Diego, CA (US)

(72) Inventors: Ming Xiao, Huntingdon Valley, PA (US); Han Cao, San Diego, CA (US)

(73) Assignee: BioNano Genomics, Inc., Philadelphia, PA (US)

( * ) Notice: Subject to any disclaimer, the term of this patent is extended or adjusted under 35 U.S.C. 154(b) by 99 days.

This patent is subject to a terminal disclaimer.

(21) Appl. No.: 13/765,353

(22) Filed: Feb. 12, 2013

(65) Prior Publication Data

US 2013/0240357 A1  Sep. 19, 2013

Related U.S. Application Data

(63) Continuation of application No. 13/001,697, filed as application No. PCT/US2009/049244 on Jun. 30, 2009, now Pat. No. 8,628,919.

(60) Provisional application No. 61/076,785, filed on Jun. 30, 2008.

(51) Int. Cl.
  *C12Q 1/68* (2006.01)
  *C12M 1/34* (2006.01)
  *C07H 21/02* (2006.01)
  *C07H 21/04* (2006.01)
  *G06F 19/18* (2011.01)

(52) U.S. Cl.
  CPC ............ *G06F 19/18* (2013.01); *C12Q 1/6806* (2013.01); *C12Q 1/6869* (2013.01)

(58) Field of Classification Search
  USPC ...... 435/6.1, 287.2; 536/23.1, 24.3; 977/704
  See application file for complete search history.

(56) References Cited

U.S. PATENT DOCUMENTS

| | | |
|---|---|---|
| 5,079,169 A | 1/1992 | Chu et al. |
| 5,314,829 A | 5/1994 | Coles |
| 5,356,776 A | 10/1994 | Kambara et al. |
| 5,405,519 A | 4/1995 | Schwartz |
| 5,427,663 A | 6/1995 | Austin et al. |
| 5,599,664 A | 2/1997 | Schwartz |
| 5,637,458 A | 6/1997 | Frankel et al. |
| 5,720,928 A | 2/1998 | Schwartz |
| 5,837,115 A | 11/1998 | Austin et al. |
| 5,867,266 A | 2/1999 | Craighead |
| 5,912,126 A | 6/1999 | Darzynkiewicz |
| 6,117,634 A | 9/2000 | Langmore |
| 6,147,198 A | 11/2000 | Schwartz |
| 6,150,089 A | 11/2000 | Schwartz |
| 6,174,671 B1 | 1/2001 | Anantharaman et al. |
| 6,197,557 B1 | 3/2001 | Makarov et al. |
| 6,210,896 B1 | 4/2001 | Chan et al. |
| 6,214,246 B1 | 4/2001 | Craighead |
| 6,221,592 B1 | 4/2001 | Schwartz et al. |
| 6,263,286 B1 | 7/2001 | Gilmanshin et al. |
| 6,340,567 B1 | 1/2002 | Schwartz et al. |
| 6,344,319 B1 | 2/2002 | Bensimon et al. |
| 6,355,420 B1 | 3/2002 | Chan |
| 6,403,311 B1 | 6/2002 | Chan |
| 6,438,279 B1 | 8/2002 | Craighead et al. |
| 6,464,842 B1 | 10/2002 | Golovchenko et al. |
| 6,607,888 B2 | 8/2003 | Schwartz et al. |
| 6,627,067 B1 | 9/2003 | Branton et al. |
| 6,635,163 B1 | 10/2003 | Han et al. |
| 6,696,022 B1 | 2/2004 | Chan et al. |
| 6,753,200 B2 | 6/2004 | Craighead et al. |
| 6,762,059 B2 | 7/2004 | Chan et al. |
| 6,772,070 B2 | 8/2004 | Gilmanshin et al. |
| 6,790,671 B1 | 9/2004 | Austin |
| 6,927,065 B2 | 8/2005 | Chan et al. |
| 7,217,562 B2 | 5/2007 | Cao et al. |
| 7,262,859 B2 | 8/2007 | Larson et al. |
| 7,282,330 B2 | 10/2007 | Zhao et al. |
| 7,312,033 B2 | 12/2007 | Accola et al. |
| 7,316,769 B2 | 1/2008 | Craighead et al. |
| 7,351,538 B2 | 4/2008 | Fuchs et al. |
| 7,371,520 B2 | 5/2008 | Zhao et al. |
| 7,402,422 B2 | 7/2008 | Fuchs et al. |
| 7,427,343 B2 | 9/2008 | Han et al. |
| 7,670,770 B2 | 3/2010 | Chou et al. |

(Continued)

FOREIGN PATENT DOCUMENTS

| | | |
|---|---|---|
| CN | 1379857 A | 11/2002 |
| EP | 0 497 272 A1 | 8/1992 |

(Continued)

OTHER PUBLICATIONS

Fu D-J et al., "Sequencing Double-Stranded DNA by Strand Displacement", Nucleic Acids Research, Information Retrieval Ltd., vol. 25, No. 3, (Jan. 1997), pp. 677-679.
Extended European Search Report for European patent application No. 13179160.0 mailed on Oct. 22, 2013.
European Office Action for European patent application No. 09774334.8 mailed on Oct. 18, 2013.
Cai et al., "High-resolution restriction maps of bacterial artificial chromosomes constructed by optical mapping." Proc. Natl. Acad. Sci. USA, vol. 95, No. 7, pp. 3390-3395 (1998).
Cao et al., "Fabrication of 10nm enclosed nanofluidic channels." Appl. Phys. Lett., 81:174-176 (2002).
Cao et al., "Gradient nanostructures for interfacing microfluidics and nanofluidics." Appl. Phys. Lett., 81:3058-3060 (2002).

(Continued)

*Primary Examiner* — Narayan Bhat
(74) *Attorney, Agent, or Firm* — Knobbe, Martens, Olson & Bear, LLP

(57) ABSTRACT

Provided are methods and devices for single-molecule genomic analysis. In one embodiment, the methods entail processing a double-stranded nucleic acid and characterizing said nucleic acid. These methods are useful in, e.g. determining structural variations and copy number variations between individuals.

23 Claims, 11 Drawing Sheets

(56) References Cited

U.S. PATENT DOCUMENTS

| | | | |
|---|---|---|---|
| 7,771,944 B2 | 8/2010 | Xiao et al. | |
| 7,775,368 B2 | 8/2010 | Schwartz et al. | |
| 7,831,392 B2 | 11/2010 | Antoniotti et al. | |
| 7,833,398 B2 | 11/2010 | Craighead et al. | |
| 7,918,979 B2 | 4/2011 | Han et al. | |
| 7,960,105 B2 | 6/2011 | Schwartz et al. | |
| 8,137,569 B2 | 3/2012 | Harnack et al. | |
| 8,168,380 B2 | 5/2012 | Chan et al. | |
| 8,663,780 B2 | 3/2014 | Harnack et al. | |
| 8,722,327 B2 | 5/2014 | Cao et al. | |
| 9,061,901 B2 | 6/2015 | Cao et al. | |
| 2001/0055764 A1 | 12/2001 | Empedocles et al. | |
| 2002/0110818 A1 | 8/2002 | Chan | |
| 2002/0119455 A1 | 8/2002 | Chan | |
| 2002/0123063 A1 | 9/2002 | Gjerde et al. | |
| 2002/0197639 A1* | 12/2002 | Shia et al. | 435/6 |
| 2003/0059822 A1* | 3/2003 | Chan et al. | 435/6 |
| 2003/0066749 A1 | 4/2003 | Golovchenko et al. | |
| 2003/0104428 A1 | 6/2003 | Branton et al. | |
| 2003/0162181 A1* | 8/2003 | Yang et al. | 435/6 |
| 2003/0209314 A1 | 11/2003 | Guo et al. | |
| 2003/0219792 A1 | 11/2003 | Armes et al. | |
| 2003/0219805 A1 | 11/2003 | Kelman et al. | |
| 2003/0232346 A1 | 12/2003 | Su | |
| 2003/0234854 A1 | 12/2003 | Hattori | |
| 2003/0235854 A1 | 12/2003 | Chan et al. | |
| 2004/0009612 A1 | 1/2004 | Zhao et al. | |
| 2004/0033515 A1 | 2/2004 | Cao et al. | |
| 2004/0166025 A1 | 8/2004 | Chan | |
| 2004/0195098 A1 | 10/2004 | Broadley et al. | |
| 2004/0197843 A1 | 10/2004 | Chou et al. | |
| 2005/0082204 A1 | 4/2005 | Schwartz et al. | |
| 2005/0208538 A1 | 9/2005 | Kurn et al. | |
| 2005/0234656 A1 | 10/2005 | Schwartz et al. | |
| 2005/0250117 A1 | 11/2005 | Su et al. | |
| 2006/0011862 A1 | 1/2006 | Bernstein | |
| 2006/0014181 A1 | 1/2006 | Barton | |
| 2006/0068440 A1 | 3/2006 | Chan et al. | |
| 2006/0088944 A1 | 4/2006 | Schwartz et al. | |
| 2006/0199202 A1 | 9/2006 | Lyamichev et al. | |
| 2006/0275806 A1 | 12/2006 | Schwartz et al. | |
| 2006/0275911 A1 | 12/2006 | Wang et al. | |
| 2007/0128083 A1 | 6/2007 | Yantz | |
| 2007/0161028 A1 | 7/2007 | Schwartz et al. | |
| 2007/0219367 A1 | 9/2007 | Shchepinov et al. | |
| 2008/0003689 A1 | 1/2008 | Lee | |
| 2008/0085552 A1 | 4/2008 | Larson et al. | |
| 2008/0103296 A1 | 5/2008 | Zhao | |
| 2008/0242556 A1 | 10/2008 | Cao et al. | |
| 2008/0254549 A1 | 10/2008 | Fuchs | |
| 2009/0076735 A1 | 3/2009 | Briska et al. | |
| 2009/0104611 A1 | 4/2009 | Schwartz et al. | |
| 2009/0208950 A1 | 8/2009 | Briska | |
| 2009/0317804 A1 | 12/2009 | Briska | |
| 2010/0028886 A1 | 2/2010 | Briska | |
| 2011/0171634 A1 | 7/2011 | Xiao et al. | |
| 2011/0171741 A1 | 7/2011 | Wang et al. | |
| 2011/0210272 A1 | 9/2011 | Chan et al. | |
| 2011/0306504 A1 | 12/2011 | Xiao et al. | |
| 2012/0196382 A1 | 8/2012 | Chan et al. | |
| 2012/0217161 A1 | 8/2012 | Chan et al. | |
| 2012/0237936 A1 | 9/2012 | Xiao et al. | |
| 2013/0177902 A1 | 7/2013 | Xiao et al. | |
| 2014/0030705 A1 | 1/2014 | Deshpande et al. | |
| 2014/0221218 A1 | 8/2014 | Cao et al. | |
| 2014/0249039 A1 | 9/2014 | Cao et al. | |
| 2015/0323518 A1 | 11/2015 | Cao et al. | |
| 2015/0368706 A1 | 12/2015 | Cao et al. | |
| 2016/0097092 A1 | 4/2016 | Xiao et al. | |
| 2016/0168621 A1 | 6/2016 | Xiao et al. | |

FOREIGN PATENT DOCUMENTS

| | | |
|---|---|---|
| JP | 2001-507929 | 6/2001 |
| JP | 2003-507026 | 2/2003 |
| JP | 2004-147658 | 5/2004 |
| JP | 2005-505754 | 2/2005 |
| JP | 2005-518215 | 6/2005 |
| JP | 2005-524413 | 8/2005 |
| JP | 2005-527220 | 9/2005 |
| JP | 2005-532822 | 11/2005 |
| JP | 2005-533636 | 11/2005 |
| JP | 2006-521786 | 9/2006 |
| JP | 2007-500363 | 1/2007 |
| WO | WO 98/39485 | 9/1997 |
| WO | WO 98/35012 | 8/1998 |
| WO | WO 00/79257 | 12/2000 |
| WO | WO 01/09184 | 2/2001 |
| WO | WO 01/13088 | 2/2001 |
| WO | WO 0113088 A1 | 2/2001 |
| WO | WO 02/65138 | 8/2002 |
| WO | WO 02/099398 | 12/2002 |
| WO | WO02/099398 | 12/2002 |
| WO | WO 02/101095 | 12/2002 |
| WO | WO 03/010289 A2 | 2/2003 |
| WO | WO 03/072805 A2 | 9/2003 |
| WO | WO 03/106620 A2 | 12/2003 |
| WO | WO 03/106693 | 12/2003 |
| WO | WO 2005/065321 | 7/2005 |
| WO | WO2005078137 | 8/2005 |
| WO | WO 2005078137 | 8/2005 |
| WO | WO 2006/102321 | 9/2006 |
| WO | WO 2007/065025 | 6/2007 |
| WO | WO 2008/076948 | 6/2008 |
| WO | WO 2010/002883 | 6/2009 |
| WO | WO 2010/002883 | 1/2010 |
| WO | WO 2010/053980 | 5/2010 |
| WO | WO 2010/059731 A2 | 5/2010 |
| WO | WO 2011/050147 | 4/2011 |

OTHER PUBLICATIONS

Castro et al., "Single-molecule detection of specific nucleic acid sequences in unamplified genomic DNA." Analytical Chemistry, 69(19):3915-3920 (1997).

Olivier et al., "High-throughput genotyping of single nucleotide polymorphisms using new biplex invader technology." Nucleic Acids Research, vol. 30, No. 12, p. E53 (2002).

Piepenburg et al., "DNA detection using recombination proteins." PLOS Biology, vol. 4, No. 7, e204 (2006).

Reccius et al., "Compression and free expansion of single DNA molecules in nanochannels." Physical Review Letters, 95:268101-1 (2005).

Tegenfeldt et al., "From the Cover: The dynamics of genomic-length DNA molecules in 100-nm channels." Proc. Natl. Acad. Sci. USA, 101(30):10979-83 (2004).

International Search Report dated Apr. 7, 2011 for PCT Application No. PCT/US2010/053513 filed Oct. 21, 2010.

Written Opinion of International Search Authority dated Apr. 21, 2011 for PCT Application No. PCT/US2010/053513 filed Oct. 21, 2010.

Xiao et al., "Rapid DNA mapping by fluorescent single molecule detection." Nucleic Acids Research, 35(e16):1-12 (2007).

International Search Report and Written Opinion of International Search Authority dated Oct. 9, 2010 for PCT Application No. PCT/US2009/049244 filed Jun. 30, 2009.

Kuhn et al., "Labeling of unique sequences in double-stranded DNA at sites of vicinal nicks generated by nicking endonucleases." Nucleic Acids Research, 36(7):e40:1-10 (2008).

Jo et al., "A single-molecule barcoding system using nanoslits for DNA analysis." Proc. Natl. Acad. Sci., 104(8):2673-2678 (2007).

Chan et al., "DNA mapping using microfluidic stretching and single-molecule detection of fluorescent site-specific tags." Genome Research, 14(6):1137-1146 (2004).

Phillips et al., "Application of single molecule technology to rapidly map long DNA and study the conformation of stretched DNA." Nucleic Acids Research, 33(18):5829-5837 (2005).

Written Opinion and Search Report of Intellectual Property Office of Singapore dated Jan. 9, 2013 for Singapore Patent Application No. 201009665-0 filed Jun. 30, 2009.

(56) References Cited

OTHER PUBLICATIONS

Das et al., "Single molecule linear analysis of DNA in nano-channel labeled with sequence specific fluorescent probes", Nucleic Acids Research, 2010, vol. 38, No. 18, 8 pages.
Notice of Allowance dated Sep. 18, 2013 in U.S. Appl. No. 13/001,697.
Office Action in U.S. Appl. No. 13/710,180, mailed Mar. 14, 2014.
Office Action for Japanese Patent Application No. 2011-516813 dated Jan. 14, 2014 by Japanese Patent Office.
Office Action for Chinese Patent Application No. 200980125335.3 dated Feb. 24, 2014 by Chinese Patent Office.
European Office Action for European Patent Application No. 09774334.8 mailed on Aug. 28, 2014.
European Search Report for European Application No. EP 12194842.6 mailed on May 31, 2013.
European Office Action for European Patent Application No. 09760398.9 mailed on Aug. 14, 2012.
European Office Action for European Application No. 08744609.2 mailed on Jul. 23, 2012.
European Office Action for European Application No. 08744609.2 mailed on Dec. 23, 2010.
European Extended Search Report for European Patent Application No. 13150068.8 mailed on Jun. 18, 2014.
European Partial Search Report for European Application No. EP 13150068.8 mailed Feb. 5, 2014.
Japanese Office Action for Japanese Patent Application No. 2011-516813 mailed on Oct. 14, 2014.
Japanese Final Office Action for Japanese Application 2010-501259 mailed Aug. 13, 2013.
Japanese Office Action for Japanese Application 2010-501259 mailed on Sep. 25, 2012.
Japanese Office Action for Japanese Patent Application No. 2011-537585 mailed on May 13, 2014.
Chinese Office Action for Chinese Patent Application No. 200880017550.7 mailed on Jun. 29, 2012.
Chinese Office Action for Chinese Patent Application No. 200980154567 mailed on Mar. 13, 2013.
Chinese Office Action for Chinese Patent Application No. 200980154567.1 mailed on Nov. 21, 2013.
Chinese Office Action for Chinese Patent Application No. 201310189106.6 mailed on Feb. 26, 2014.
Chinese Office Action for Chinese Patent Application No. 201310189106.6 mailed on Nov. 14, 2014.
Chinese Office Action for Chinese Patent Application No. 200880017550.7 mailed on Nov. 14, 2012.
Australian Office Action for Australian Application No. 2008232616 mailed on Nov. 9, 2012.
Canadian Office Action for Canadian Patent Application No. 2682275 mailed on Sep. 29, 2014.
Korean Office Action for Korean Patent Application No. 10-2009-7022447 mailed on Aug. 12, 2014.
International Search Report for International Application No. PCT/US2009/064996 mailed on Aug. 16, 2010.
International Search Report and Written Opinion for PCT Application No. PCT/US2008/058671 mailed on Jan. 19, 2009.
Vaandrager J W et al., "DNA fiber fluorescence in situ hybridization analysis of immunoglobulin class switching in B-cell neoplasia: aberrant CH gene rearrangements in follicle center-cell lymphoma", BLOOD, Oct. 15, 1998, vol. 92, No. 8, pp. 2871-2878.
Amann R et al., "In situ visualization of high genetic diversity in a natural microbial community", Journal of Bacteriology, American Society for Microbiology, Washington, DC; US, vol. 178, No. 12, Jun. 1, 1996, pp. 3496-3500.
Reil Heide et al., "Clinical validation of a new triplex real-time polymerase chain reaction assay for the detection and discrimination of Herpes simplex virus types 1 and 2", The Journal of Molecular Diagnostics: Jul. 2008, vol. 10, No. 4, pp. 361-367.
Slater, et al., "Bidirectional Transport of Polyelectrolytes Using Self-Modulating Entropic Ratchets," Physical Review Letters, The American Physical Society, 78(6), Feb. 1997, 1170-1173.

W. Volkmuth et al.: "Observation of Electrophoresis of Sincle DNA Molecules in Nanofabricated Arrays", American Society for Biochemistry and Molecular Biology Biophysical Society Joint Meeting, Houston Texas, Feb. 9-13, 1992, Abstracts, FASEB Journal, vol. 6, No. 1, Jan. 1, 1992. 3 pages.
Austin et al.: "Scanning the Controls: Genomics and Nanotechnogloy," IEEE Transactions on Nanotechnology 1: 12-18, 2002.
Cai et al.: "Ordered restriction endonuclease maps of artificial chromosomes created by optical mapping on surfaces," PNAS 92: 5164-8, 1995.
Chang et al.: "DNA-Mediated Fluctuations in Ionic Current through Silicon Oxide Nanopore Channels," Nano Letters 4: 1551-1556, 2004.
Chen et al.: "Atomic Layer Deposition to Fine-Tune the surface Properties and Diameters of Fabricated Nanopores," Nano Letters 4: 1333-1337, 2004.
Chen et al.: "Probing Single DNA Molecule Transport Using Fabricated Nanopores," Nano Letters 4: 2293-2298, 2004.
Chou et al.: "A Microfabricated Device for Sizing and Sorting DNA Molecules," Proc. Natl. Acad. Sci. USA, Jan. 1999, 96, 11-13.
Conrad et al.: "A high-resolution survey of deletion polymorphism in the human genome," Nature Genetics 38: 75-81, 2006.
Czaplewski et al.: "Nanofluidic channels with elliptical cross sections formed using a nonlithographic process," Applied Physics Letters, Dec. 8, 2003, 83(23), 836-4838.
Deamer et al.: "Characterization of Nucleic Acids by Nanopore Analysis," Acc Chem Res 35: 817-825, 2002.
Deegan et al.: "Contact line deposits in an evaporating drop," Physical Review E, Jul. 2000, 62(1), 756-765.
Dietrich et al.: "Advances in the Development of a Novel Method to be used in Proteomics using Gold Nanobeads," U/trasens/tive and Single-Molecule etection Technologies, edited by Jorg Enderlein, et al, Proc. of SPIE vol. 6092, 6092C (2006).
Eichler: "Widening the spectrum of human genetic variation," Nature Genetics 38: 9-11, 2006.
Examination Report dated Jul. 23, 2012 for European Application No. 08744609.2.
FDA Redbook 2000 Genotoxicity Tests, available at www.cfsan.fda.gov.
Gad et al.: "Bar code screening on combed DNA for large rearagements of the BRCA1 and BRCA2 genes in French breast cancerfami l ies." J Med Genet 39: 17-21, 2002.
Gad et al.: "Color bar coding the BRCA1 gene on combed DNA: A useful strategy for detecting large gene arrangements." Genes, Chromosomes and Cancer 31: 5-84, 2001.
Gracheva et al.: "Simulation of the electric response of DNA translocation through a semiconductor nanopore-capacitor," Nanotechnology 17: 622-633, 2006.
Guidance for industry S2B Genotoxicity: A standard Battery for Genotoxicity Testing of Pharmaceuticals, Jul. 1997, ICH.
Guo et al: "Fabrication of Size-Controllable Nanofluidic Channels by Nanoimprinting and its Application for DNA Stretching", 2004, 4, 69-73.
Hashioka et al.: "Simple and Quick Detection of Target DNA by Hybridization in Nano Gap Channel Array." 9th International Conference on Miniaturized Systems or Chemistry and Life Sciences, vol. 1, pp. 730-732 (2005).
Henriquez et al.: "The resurgence of Coulter counting for analyzing nanoscale objects," The Analyst, 2004, 129, 478-482.
Hinds et al.: "Common deletions and SNPs are in linkage disequilibrium in the human genome," Nature Genetics 38: 82-85, 2006.
Howorka et al.: "Kinetics of duplex formation for individual DNA strands within a single protein nanopore," PNAS 98: 12996-13001, 2001.
Howorka et al.: "Sequence-specific detection of individual DNA strands using engineered nanopores," Nature Biotechnology 19: 636-639, 2001.
International Preliminary Report on Patentability dated Feb. 23, 2009 for PCT Application No. PCT/US2007/016408.
International Search Report dated Aug. 17, 2012 for Application PCT/US2011/057115.

(56) References Cited

OTHER PUBLICATIONS

Japanese Office Action dated Jul. 24, 2012 for Japanese Patent Application No. 2009-520847 (English translation thereof is enclosed).
Johansson et al.: "Primary vs. secondary neoplasia-associated chromosomal abnormalities-balanced rearrangements vs genomic imbalances?" Genes, Chromosomes and Cancer 16: 155-163, 1996.
Kasianowicz et al.: "Characterization of individual polynucleotide molecules using a membrane channe l," PNAS 93: 13770-13773, 1996.
Koppal et al.: "Spanning the Drug Pipeline," Drug Discovery & Development, Sep. 13, 2005, 1 page, http://www.dddmag.com.
Li et al.: "Ion-beam sculpting at nanometer length scales," Nature 412: 166-169, 2001.
Li et al.: "DNA molecules and configurations in a solid-state nanopore microscope," Nature Materials 2: 611-615, 2003.
Li, et al.: "Sacrificial polymers for nanofluid channels in biological applications," Nanotechnology, 2003, 14, 578-583.
Mannion et al., Conformational Analysis of Single DNA Molecule Undergoing Entropically Induced Motion in Nanochannels, Biophysical Journal, Jun. 2006, vol. 90, pp. 4538-4545.
McCarroll et al.: "Common deletion polymorphisms in the human genome," Nature Genetics 38: 86-92, 2006.
McGee et al.: "New in Vitro, Modeling Tools May Cut Tox Attrition," Drug Discovery & Development, Aug. 4, 2005, 4 pages, http://wvvw.dddmag.com.
McGee, et al.: "Small-Animal Models Advance in Vivo ADME-Tox", Drug Discovery & Development, Jul. 5, 2005, 3 pages, http://wvvw.dddmag.com.
Meller et al.: "Rapid nanopore discrimination between single polynucleotide molecules," PNAS 97: 1079-1084, 2001.
Meller et al.: "Voltage-Driven DNA Translocations through a Nanopore," Physical Review Letters 86: 3435-3438, 2001.
Meng et al.: "Optical mapping of lambda bacteriophage clones using restriction endonucleases," Nat Genet 9: 432-438, 1995.
Mijatovic et al., "Technologies for nanoflui di csystems: top-down vs. bottom-up—a review," Lab on a Chip, Royal Society of Chemistry, Cambridge, GB, Jan. 2005, vol. 5, 492-500.
Molecular Devices website, product page For Axopatch 200B: No date present NB/http://wvvw.moleculardevices.com/pages/instruments/cn_axopatch200b.html.
Nagata et al.: "Degradation of chromosomal DNA during apoptosis," Cell Death and Differentiation 10: 108-116, 2003.
Nath et al.: "A System for Micro/Nano Fluidic Flow", Diagnostics, 2005, Biomedical Microdevices, 7, 169-177.
Notice of Allowance dated Dec. 11, 2013 for Canadian Patent Application No. 2658122.
Notice of Allowance dated Jan. 23, 2014 for Australian Patent Application No. 2007338862.
Office Action dated Aug. 12, 2014 issued in Korean Patent Application No. 10-2009-7022447.
Office Action dated Dec. 9, 2013 for Japanese Patent Application No. 2009-520847.
Office Action dated Feb. 5, 2013 for Japanese Patent Application No. 2009-520847.
Office Action dated Jan. 4, 2012 for Chinese Patent Application No. 200780034694.9.
Office Action dated Jan. 7, 2015 for Australian Patent Application No. 2011316989.
Office Action dated Mar. 25, 2014 in Chinese Patent Application No. 201310054745.1.
Office Action dated Dec. 18, 2014 in Chinese Patent Application No. 201180060380.2.
Office Action dated Mar. 28, 2013 for Canadian Patent Application No. 2658122.
Office Action dated May 9, 2012 for Australian Patent Application No. 2007338862.
Office Action dated May 9, 2012 of U.S. Appl. No. 13/001,697.
Office Action dated Nov. 14, 2014 for Chinese Patent Application No. 201310189106.6.
Office Action dated Nov. 5, 2012 for Chinese Patent Application No. 200780034694.9.
Office Action dated Jan. 20, 2015 for Japanese Patent Application No. 2013-258107.
Office Action in U.S. Appl. No. 13/880,365, mailed Dec. 8, 2014.
Office Action dated Jan. 30, 2015 for Korean patent application No. 10-2011-7000192.
Office Action dated Apr. 15, 2015 for Canadian Patent Application No. 2682275.
Purves et al.: "Genotoxicity testing: Current Practices and Strategies Used by the Pharmaceutical l ndustry," Mutagenesis, 1995, vol. 10 No. 4 pp. 297-312.
Turner, et al.: "Monolithic nanofluid sieving structures for DNA manipulation", Journal of Vacuum Science and Technology, 16, 3835, 1998.
Storm et al.: "Fabrication of solid-state nanopores with single-nanometer precision," Nature Materials 2: 537-540, 2003.
Storm et al.: "Fast DNA Translocation through a Solid-State Nanopore," Nano Letters 5: 1193-1197, 2005.
Technology Research News, LLC, "Melted fibers make nano channels," Jan. 14, 2004, Retrieved from the internet at URL <http://wvvw.trnmag.com/Stories/2004/011404/Me l ted_fibers_make_nano_channe l s_Brief.
Tegenfeldt et al.: "Micro and nanofluidics for DNA analysis," Anal Bioanal Chem 378: 1678-1692, 2004.
Tegenfeldt et al.: "The dynamics ofgenomic-length DNA molecules in 100-nm channe l s," PNAS 101: 10979-10983, 2004b.
Volkmuth et al.: "DNA electrophoresis in microlithographic arrays", Department of Physics, Princeton University, Nature, vol. 358, Aug. 13, 1992, pp. 600-602.
Wade et al.: "The Quest for the $1,000 Human Genome" The New York Times, Jul. 18, 2006.
Wong et al.: "Deformation of DNA molecules by hydrodynamic focusing," J Fluid Mechanics 497: 55-65, 2003.
Kaufman et al.: "Early S phase DNA replication: A search for target of carcinogenesis" Advan. Enzyme Regul. 2007, 47: 127-138.
Pfannschmidt et al., Jan. 30, 1998, Superhelix organization by DNA curvature as measured through site-specific labeling, Journal of Molecular Biology, 275(4):601-611.
Rigby et al., Jun. 15, 2977, Labeling deoxyribonucleic acid to hight specific activity in vitro by nick translation with DNA polymerase 1, Journal of Molecular Biology, 113(1):237-251.
Second Office Action dated Dec. 9, 2014 in Chinese Patent Application No. 201310054745.1.
Office Action dated Jul. 7, 2015 in Japanese patent application No. 2014-089510.
Office Action dated Apr. 16, 2015 in U.S. Appl. No. 14/195,474.
Office Action dated Nov. 27, 2015 for Canadian Patent Application No. 2682275.
Office Action dated May 29, 2015 for Chinese Patent Application No. 201310189106.6.
Decision of Patent Grant dated Nov. 24, 2015 for Japanese Patent Application No. 2013-258107.
Office Action dated Sep. 17, 2014 for Chinese Patent Application No. 200980125335.3.
Office Action dated Apr. 3, 2015 for Chinese Patent Application No. 200980125335.3.
Examination Report dated Dec. 15, 2015 in European patent application No. 09774334.8.
Examination Report dated Dec. 15, 2015 for European patent application No. 13179160.0.
Office Action dated Oct. 25, 2013, in U.S. Appl. No. 13/129,634.
Office Action dated Jun. 6, 2014, in U.S. Appl. No. 13/129,634.
Office Action dated Jan. 2, 2015 in U.S. Appl. No. 13/129,634.
Patent Examination Report No. 1 dated Aug. 21, 2015 in Australian Appl. No. 2009316628.
Canadian Official Action dated Nov. 4, 2015 in Canadian patent application No. 2,744,064.
Second Office Action dated Sep. 11, 2015 in Chinese Patent Application No. 201180060380.2.
Examination Report dated Jun. 24, 2015 in European patent application No. 11777008.1.

(56) References Cited

OTHER PUBLICATIONS

Office Action dated Nov. 17, 2015 in Japanese patent application No. 2013-535092.
Office Action in U.S. Appl. No. 13/880,365, dated May 4, 2015.
Office Action dated Dec. 15, 2015 in U.S. Appl. No. 13/880,365.
Notification on Non-Compliance with the Unity of Invention Requirement dated Sep. 7, 2015 in Russian patent application No. 2013117936.
Office Action dated Jul. 14, 2015 in U.S. Appl. No. 13/710,180.
Official Action dated Dec. 22, 2014 in Russian patent application No. 2012116604.
Chen et al., 2007, A Microfluidic System for Saliva-Based Detection of infectious Diseases, Ann. N.Y. Acad. Sci., 1098:429-436.
Examination Report dated Feb. 1, 2016 in European patent application No. 07872156.0.
Notice of Reasons for Refusal dated May 10, 2016 in Japanese patent application No. 2014-089510.
Patent Examination Report No. 1 dated Feb. 12, 2016 in Australian patent application No. 2014256367.
Office Action dated Feb. 15, 2016 for Chinese Patent Application No. 201310189106.6.
Examination Report dated May 5, 2015 in Canadian patent application No. 2729159.
Office Action dated Jan. 5, 2016 for Chinese Patent Application No. 200980125335.3.
Office Action dated Jul. 5, 2016 for Chinese Patent Application No. 200980125336.3.
Notice of Reasons for Refusal dated Feb. 23, 2016 in Japanese patent application No. 2015-078505.
Patent Examination Report No. 2 dated Feb. 8, 2016 in Australian patent application No. 2011316989.
Office Action dated Jul. 11, 2016 in U.S. Appl. No. 13/880,365.
Official Action (Request) dated Jan. 28, 2016 in Russian patent application No. 2013117936.
Office Action dated Aug. 12, 2016 in European Application No. 13179160.0.
Office Action dated Aug. 24, 2016 in Japanese Application No. 2015-078505 with English Translation.

* cited by examiner

First, Generate Flap Sequences by nicking and displacing downstream strand

Flap generation

Hybridization of fluorescent sequence specific probe at one site

A tagging agent A, B or C are associated with the extended DNA during incorporation or hybridization; a co-localization event could be detected by a specific Fluorescent Resonance Energy Transfer (FRET) signal.

*In silico* Nicking sites on lambda ds-DNA (48.5 kbp total length)

*Observed* Nicking sites on lambda ds-DNA (48.5 kbp total length)

Similar barcode results shown on linearized human BAC clone DNAs with complete stretching (~170 Kb); over 17 labeled sites (in fluorescent color) are shown here.

Epigenetic patterns overlay with genomic location patterns in real time

FIG. 6A  NanoAnalyzer[R] Genome Assembly Scaffolding Application
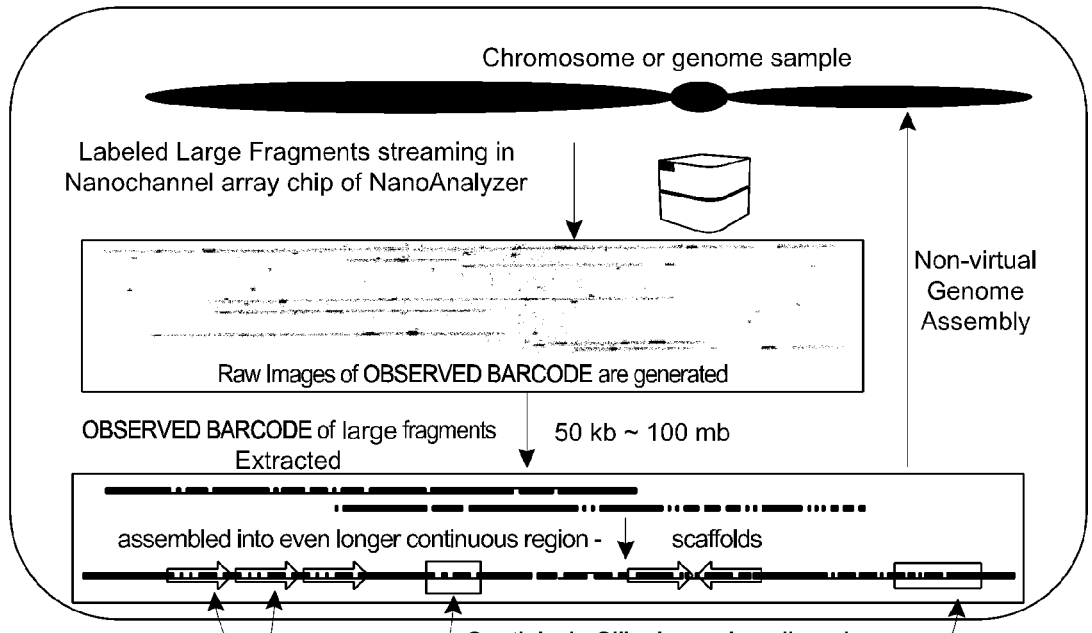
FIG. 6B
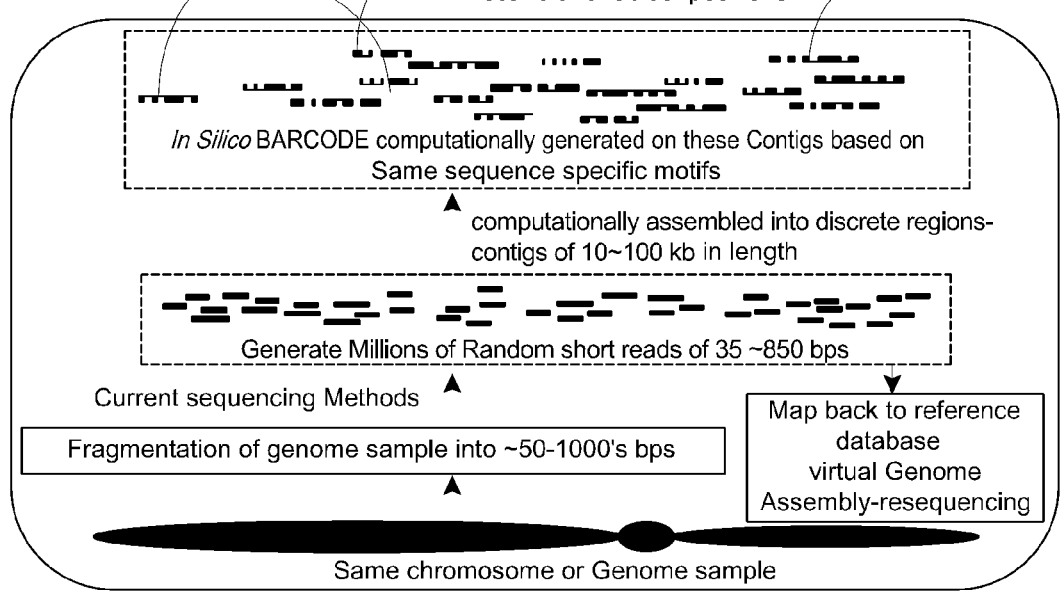

Imaging Analysis
automatic DNA detection and sizing

FIG. 8A  Optical and non-optical detection schemes  FIG. 8B
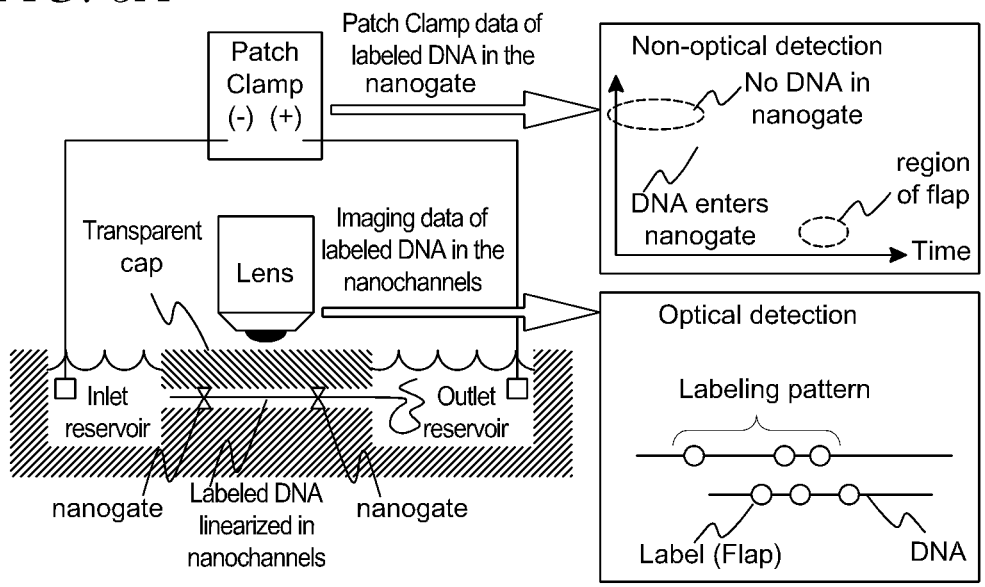
FIG. 8C
FIG. 8D
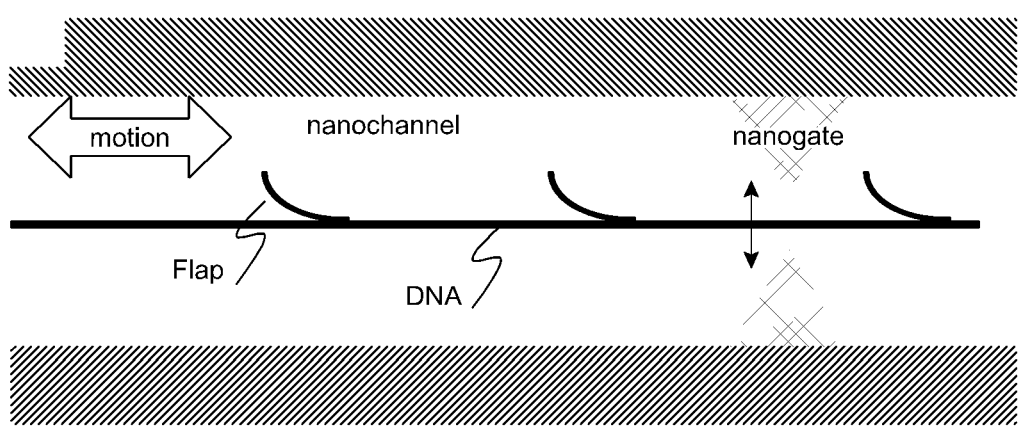

R1=nucleic acid (ss-DNA, ds-DNA, RNA)
R2=sequence being analyzed with analysis proceeding at multiple points
R3=modification to permit tethering R=chemical modification
A=region of attachment which may have surface chemical modification

FIG. 11A

Magnetic modification for tethering nucleic acid

Tethering at entrance to channel

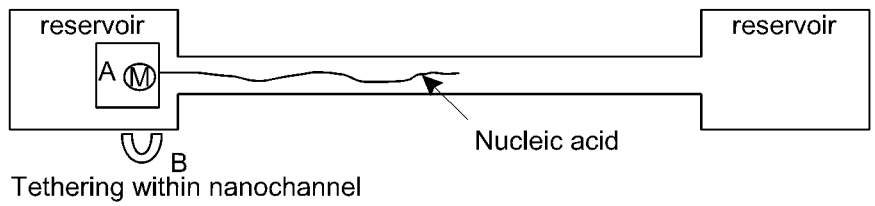

Tethering within nanochannel

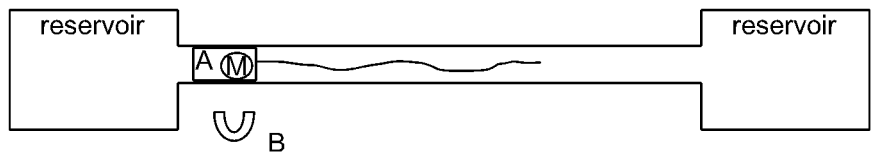

M= magnetic modification
A=on-chip magnetic field for tethering
B=externally applied magnetic field for tethering

FIG. 11B

Optical trapping for tethering nucleic acid

Tethering at entrance to channel

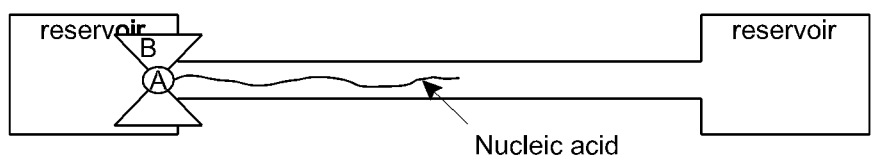

Tethering within nanochannel

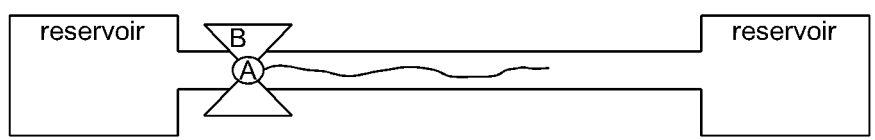

A=dielectric modification
B=field of optical trap

SEQUENCE LISTING

```
<160> NUMBER OF SEQ ID NOS: 15

<210> SEQ ID NO 1
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 1
tgaggtttgc accggtgtgg ctccggaagt taacgctaaa gcactggcct g            51

<210> SEQ ID NO 2
<211> LENGTH: 77
<212> TYPE: DNA
<213> ORGANISM: Artificial Sequence
<220> FEATURE:
<223> OTHER INFORMATION: Synthetic polynucleotide

<400> SEQUENCE: 2
caccctgctt gctgaggttt gcaccggtgt ggctccggaa gttaacgcta aagcactggc   60
ctggggaaaa cagtacg                                                  77
```

```
<210> SEQ ID NO 3
<211> LENGTH: 76
<212> TYPE: DNA
<213> ORGANISM: Artificial Sequence
<220> FEATURE:
<223> OTHER INFORMATION: Synthetic polynucleotide

<400> SEQUENCE: 3
cgtactgttt tcccaggcca gtgctttagc gttaacttcc ggagccacac cggtgcaaac      60
ctcagcaagc agggtg                                                     76

<210> SEQ ID NO 4
<211> LENGTH: 12
<212> TYPE: DNA
<213> ORGANISM: Artificial Sequence
<220> FEATURE:
<223> OTHER INFORMATION: Synthetic polynucleotide

<400> SEQUENCE: 4
caccctgctt gc                                                         12

<210> SEQ ID NO 5
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 5
gggaaaacag tacg                                                       14

<210> SEQ ID NO 6
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 6
acgtgggaaa                                                            10

<210> SEQ ID NO 7
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 7 ggggatgta                                                              9

<210> SEQ ID NO 8
<211> LENGTH: 7
<212> TYPE: DNA
<213> ORGANISM: Artificial Sequence
<220> FEATURE:
<223> OTHER INFORMATION: Synthetic polynucleotide

<400> SEQUENCE: 8 gctgagg                                                                7

<210> SEQ ID NO 9
<211> LENGTH: 7
<212> TYPE: DNA
```

<213> ORGANISM: Artificial Sequence
<220> FEATURE:
<223> OTHER INFORMATION: Synthetic polynucleotide

<400> SEQUENCE: 9 cctcagc                                                            7

<210> SEQ ID NO 10
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 10 gctgacccc                                                          9

<210> SEQ ID NO 11
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 11 gctgacgg                                                           8

<210> SEQ ID NO 12
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 12 gctgagcgg                                                          9

<210> SEQ ID NO 13
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 13 gctgaacgt                                                          9

<210> SEQ ID NO 14
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 14 gcggccgc                                                           8

<210> SEQ ID NO 15
<211> LENGTH: 8
<212> TYPE: DNA

```
<213> ORGANISM: Artificial Sequence
<220> FEATURE:
<223> OTHER INFORMATION: Synthetic polynucleotide

<400> SEQUENCE: 15 cgcgcgcg                                                                  8
```

METHODS AND DEVICES FOR SINGLE-MOLECULE WHOLE GENOME ANALYSIS

RELATED APPLICATIONS

The present application is a continuation of U.S. application Ser. No. 13/001,697, filed Mar. 22, 2011, which is a U.S. National Phase Application of PCT/US09/49244, filed Jun. 30, 2009, which claims priority to U.S. Application No. 61/076,785, filed Jun. 30, 2008, the entirety of which are incorporated herein by reference.

FIELD OF THE INVENTION

The present invention relates to the field of nanofluidics and to the field of DNA sequencing.

BACKGROUND OF THE INVENTION

Macromolecules are long polymer chains composed of many chemical units bonded to one another. Polynucleotides are a class of macromolecules that include, for example, DNA and RNA. Polynucleotides are composed of long sequences of nucleotides.

The sequence of nucleotides is directly related to the genomic and post-genomic gene expression information of the organism. Direct sequencing and mapping of sequence regions, motifs, and functional units such as open reading frames (ORFs), untranslated regions (UTRs), exons, introns, protein factor binding sites, epigenomic sites such as CpG clusters, microRNA sites, Small interfering RNA (SiRNA) sites, large intervening non-coding RNA (lincRNA) sites and other functional units are all important in assessing the genomic composition of individuals.

In many cases, complex rearrangement of these nucleotides' sequence, such as insertions, deletions, inversions and translocations, during an individual's life span leads to disease states such as genetic abnormalities or cell malignancy. In other cases, sequence differences as in Copy Number Variations (CNVs) among individuals reflects the diversity of the genetic makeup of the population and their differential responses to environmental stimuli and signals such as drug treatments. In still other cases, processes such as DNA methylation, histone modification, chromatin folding or other changes that modify DNA or DNA-protein interactions influence gene regulations, expressions and ultimately cellular functions resulting in diseases and cancer.

It has been found that genomic structural variations (SVs) are much more widespread than previously thought, even among healthy individuals. The importance of understanding genome sequence with structural variations information to human health and common genetic disease has thus become increasingly apparent.

Functional units and common structural variations are thought to encompass from tens of bases to more than megabases. Accordingly, a method that is direct, inexpensive and yet flexible of revealing sequence information and SVs across the resolution scale from sub-kilobase to megabase along large native genomic molecules is highly desirable in sequencing and fine-scale mapping projects of more individuals in order to catalog previously uncharacterized genomic features.

Furthermore, phenotypical polymorphism or disease states of biological systems, particularly in multiploidy organism such as humans, are consequence of the interplay between the two haploid genomes inherited from maternal and paternal lineage. Cancer, in particular, is often the result of the loss of heterozygosity among diploid chromosomal lesions.

Conventional cytogenetic methods such as karyotyping, FISH (Fluorescent in situ Hybridization) provided a global view of the genomic composition in as few as a single cell, they are effective in revealing gross changes of the genome such as aneuploidy, gain, loss or rearrangements of large fragments of thousands and millions bases pairs. These methods, however, suffer from relatively low sensitivity and resolution in detecting medium to small sequence motifs or lesions. The methods are also laborious, which limits speed and inconsistency.

More recent methods for detecting sequence regions, sequence motifs of interests and SVs, such as aCGH (array Comparative Genomic Hybridization), fiberFISH or massive pair-end sequencing have improved in the aspects of resolution and throughput. These methods are nonetheless indirect, laborious, expensive and rely on existing reference databases. Further, the methods may have limited fixed resolution, and provide either inferred positional information relying on mapping back to a reference genome for reassembly or comparative intensity ratio information. Such methods are thus unable to reveal balanced lesion events such as inversions or translocations.

Current sequencing analysis approaches are limited by available technology and are largely based on samples derived from an averaged multiploidy genomic materials with very limited haplotype information. The front end sample preparation methods currently employed to extract the mixed diploid genomic material from a heterogeneous cell population effectively shred the material into smaller pieces, which results in the destruction of native the crucially important structural information of the diploid genome.

Even the more recently developed second-generation methods, though having improved throughput, further complicate the delineation of complex genomic information because of more difficult assembly from much shorter sequencing reads.

In general, short reads are more difficult to align uniquely within complex genomes, and additional sequence information are needed to decipher the linear order of the short target region.

An order of 25-fold improvement in sequencing coverage is needed to reach similar assembly confidence instead of 8-10 fold coverage needed in conventional BAC and so-called shot gun Sanger sequencing (Wendl M C, Wilson R K Aspects of coverage in medical DNA sequencing, BMC Bioinformatics, 16 May 2008; 9:239). This multi-fold sequencing coverage imposes high costs, effectively defeating the overarching goal in the field of reducing sequencing cost below the $1,000 mark.

Single molecule level analysis of large intact genomic molecules thus provides the possibility of preserving the accurate native genomic structures by fine mapping the sequence motifs in situ without cloning process or amplification. The larger the genomic fragments are, the less complex of sample population in genomic samples, for example, in ideal scenario, only 46 chromosomal length of fragments need to be analyzed at single molecule level to cover the entire normal diploid human genome and the sequence derived from such approach has intact haplotype information by nature. Further, megabase-scale genomic fragments can be extracted from cells and preserved for direct analysis, which dramatically reduces the burden of complex algorithm and assembly, also co-relates genomic and/or epigenomic information in its original context more directly to individual cellular phenotypes.

In addition to genomics, the field of epigenomics has been increasingly recognized in the past 20 years or so as being of singular importance for its roles in human diseases such as cancer. With the accumulation of knowledge in both genomics and epigenomics, a major challenge is to understand how genomic and epigenomic factors correlate directly or indirectly to develop the polymorphism or pathophysiological conditions in human diseases and malignancies. Whole genome analysis concept has evolved from a compartmentalized approach in which areas of genomic sequencing, epigenetic methylation analysis and functional genomics were studied largely in isolation, to a more and more multi-faceted holistic approach. DNA sequencing, structural variations mapping, CpG island methylation patterns, histone modifications, nucleosomal remodeling, microRNA function and transcription profiling have been increasingly viewed more closely in systematical way, however, technologies examining each of above aspects of the molecular state of the cells are often isolated, tedious and non-compatible which severely circumvent the holistic analysis with coherent experiment data results.

Accordingly, there is a need in the art for methods and devices that enable single molecule level analysis of large intact native biological samples so as to enable determination of genomic and epigenomic information of a target sample. Such methods and devices would provide a very powerful tool to researchers and clinicians alike.

SUMMARY OF THE INVENTION

In meeting the described challenges, the claimed invention first provides methods of characterizing DNA, comprising: processing a double-stranded DNA comprising a first DNA strand and a second DNA strand to give rise to an unhybridized flap of the first DNA strand and a corresponding region on the second DNA strand, the unhybridized flap comprising from about 1 to about 1000 bases; extending the first DNA strand along the corresponding region of the second DNA strand; and labeling at least a portion of the unhybridized flap, a portion of the extended first DNA strand, or both.

Also provided are methods of identifying structural variations between DNAs, comprising: labeling, on a first double-stranded DNA, two or more sequence-specific locations on the first DNA; labeling, on a second double-stranded DNA, the two or more corresponding sequence-specific locations on the second DNA; linearizing at least a portion of the first double-stranded DNA; linearizing at least a portion of the first double-stranded DNA; and comparing the distance between two or more labels on the first, linearized double-stranded DNA to the distance between the corresponding labels on the second, linearized linearized double-stranded DNA.

Further disclosed are methods of obtaining structural information from DNA, comprising: labeling, on a first double-stranded DNA, one or more sequence-specific locations on the first DNA; labeling, on a second double-stranded DNA, the corresponding one or more sequence-specific locations on the second double-stranded DNA; linearizing at least a portion of the first double-stranded DNA; linearizing at least a portion of the first double-stranded DNA; and comparing the intensity of a signal of the at least one label of the first, linearized double-stranded DNA to the intensity of the signal of the at least one label of the second, linearized double-stranded DNA.

Additionally provided are methods of obtaining structural information from a macromolecule, comprising: translocating a macromolecule comprising at least one flap extending therefrom along a channel having at least one constriction disposed therein; and detecting at least one signal corresponding to the passage of the at least one flap of the macromolecule through the at least one constriction of the channel.

Provided also are methods of obtaining structural information from a macromolecule, comprising: labeling at least a portion of a macromolecule; immobilizing the macromolecule; disposing at least a portion of the macromolecule within a channel such that at least a portion of the macromolecule is linearized within the channel; and detecting at least one signal related to the labeled portion of the macromolecule.

Also disclosed are analysis systems, comprising: a substrate comprising at least one channel having a width in the range of from about 1 to about 100 nanometers; the substrate comprising at least one immobilization region.

Further provided are methods of characterizing a nucleic acid polymer, comprising: labeling one or more regions of a nucleic acid polymer with one or more sequence-specific motif labels; correlating one or more signals from one or more of the sequence-specific motif labels to the position of the one or more sequence-specific motif labels of the nucleic acid polymer; sequencing one or more segments of the nucleic acid polymer, the one or more segments including one or more of the sequence specific motif labels of the nucleic acid polymer; and comparing one or more signals of one or more sequenced segments to one or more corresponding signals of the labeled nucleic acid polymer so as to develop the relative locations within the nucleic acid polymer, of two of more sequenced segments.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings:

FIG. 6A depicts obtaining genome assembly information from a nucleic acid polymer, including "labeled large fragments streaming in Nanochannel array chip of NanoAnalyzer," "raw images of observed barcode are generated," "observed barcode of large fragments extracted," "assembled into even longer region-scaffolds," and "non-virtual genome assembly";

FIG. 6B depicts obtaining genome assembly information from a nucleic acid polymer, "fragmentation of genome sample," "generate millions of random short reads," "map back to reference database virtual genome assembly-resequencing," "computationally assembled into discrete regions," and "in silico barcode computationally generated on these contigs based on same sequence-specific motifs";

FIG. 8A depicts optical and non-optical detection schemes according to the claimed invention, including a system for obtaining labeled barcode information from a nucleic acid polymer utilizing both optical and non-optical detection methods;

FIG. 8B depicts optical and non-optical detection schemes, including non-optical detection;

FIG. 8C depicts optical and non-optical detection schemes, including optical detection;

FIG. 8D depicts optical and non-optical detection schemes, including a nanogate-comprising fluidic device;

FIG. 11A depicts magnetic trapping of nucleic acid polymers disposed within nanochannels or nanotracks, including showing a nucleic acid molecule is magnetically modified at or near one end of the molecule.

FIG. 11B depicts optical trapping of nucleic acid polymers disposed within nanochannels or nanotracks, including showing a nucleic acid is modified at or near one end of the molecule with a particle or moiety capable of experiencing a dielectric force gradient in the presence of optical tweezers.

DETAILED DESCRIPTION OF THE PREFERRED EMBODIMENT

Figure 1A:
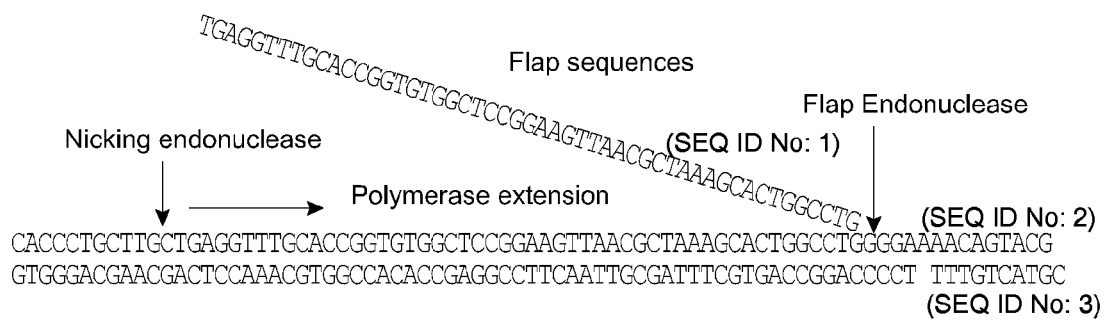
FIG. 1A depicts a schematic view of the claimed flap-labeling methods, including "First, generate flap sequences by nicking and displacing downstream strand"

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

In a first aspect, the present invention provides of characterizing DNA, comprising processing a double-stranded DNA comprising a first DNA strand and a second DNA strand to give rise to an unhybridized flap of the first DNA strand and a corresponding region on the second DNA strand, the unhybridized flap comprising from about 1 to about 1000 bases; extending the first DNA strand along the corresponding region of the second DNA strand; and labeling at least a portion of the unhybridized flap, a portion of the extended first DNA strand, or both.

The flap is suitably from about 1 to about 1000 bases in length. A flap is suitably from about 20 to about 100 bases in length, or even in the range of from about 30 to about 50 bases.

The methods also include incorporating one or more replacement bases into the first strand of double-stranded DNA so as to extend the first DNA strand (from which the flap is peeled) to fill-in and eliminate the gap (i.e., the now-corresponding region of the second DNA strand) left by formation of the flap. The user may label at least a portion of the processed double-stranded DNA (the first DNA strand, the second DNA strand, the flap, or any combination thereof) with one or more tags. The filled-in gap left by the flap can include one or more labeled portions. In some embodiments (not shown), the flap may be excised using a flap-removing enzyme, leaving behind a dsDNA having one or more nucleotides incorporated therein.

The processing is suitably accomplished by nicking the first strand of double-stranded DNA. This nicking is suitably effected at one or more sequence-specific locations, although the nicking can be effected at one or more non-specific locations, including random or non-specific locations.

Nicking is suitably accomplished by exposing the double-stranded DNA polymer to a nicking endonuclease, or nickase. Nickases are suitably highly sequence-specific, meaning that they bind to a particular sequence of bases (motif) with a high degree of specificity. Nickases are available, e.g., from New England BioLabs (www.neb.com).

The nicking may also be accomplished by other enzymes that effect a break or cut in a strand of DNA. Such breaks or nicks can also be accomplished by exposure to electromagnetic radiation {e.g., UV light), one or more free radicals, and the like. Nicks may be effected by one or more of these techniques.

Incorporation of replacement bases into the first strand (i.e., the nicked strand) of double-stranded DNA suitably comprises contacting DNA with a polymerase, one or more nucleotides, a ligase, or any combination thereof. Other methods for replacing the "peeled-away" bases present in the flap will also be known to those of ordinary skill in the art. The first DNA strand is suitably extended along the corresponding region of the second DNA, which region is left behind/exposed by the formation of the flap. In some embodiments, the polymerase acts concurrent with a nickase that gives rise to a flap.

The incorporation of these replacement bases can be conceptualized as filling-in the gap left behind by the formation and "peeling-up" of the flap. By filling in the gap, the position formerly occupied by the flap is occupied by a set of bases that suitably has the same sequence as the bases located in the flap. The filling can prevent re-hybridization of the flap to the second stand of DNA to which the flap was formerly bound.

Labeling is suitably accomplished by (a) binding at least one complementary probe to at least a portion of the flap, the probe comprising one or more tags, (b) utilizing, as a replacement base that is part of the first DNA strand extended along the corresponding region of the second DNA strand, a nucleotide comprising one or more tags, or any combination of (a) and (b). In this way, the flap, the bases that fill-in the gap, or both may be labeled.

Probes are suitably nucleic acids (single or multiple) that include a tag, as described elsewhere herein. A probe may be sequence specific (e.g., AGGCTA, or some other particular base sequence), although probes may be randomly generated. As described elsewhere herein, a probe may be selected or constructed based on the user's desire to have the probe bind to a sequence of interest or, in one alternative, bind to a sequence that up- or downstream from a sequence or other region of interest on a particular DNA polymer (i.e., probes that bind so as to flank or bracket a region of interest). A probe may be as long as a flap (i.e., up to 1000 bases). A probe is suitably in the range of from 1 to about 100 bases in length, or from about 3 to 50 bases, or even in the range of from about 5 to about 20 bases in length.

A schematic view of these methods is shown in FIG. 1. In that figure, the creation of a flap and the back-filling of the resulting gap is shown. The back-filling may be with so-called "hot" or labeled bases, and the flap may be contacted with one or more probes that are complementary to at least a portion of the flap. A sequence specific nicking endonuclease, or nickase, creates a single strand cut gap on double stranded DNA, and a polymerase binds to the nicked site and starts strand extension while generating a displaced strand or so-called "peeled flap" simultaneously. The peeled flap then creates an available region (i.e., an unhybridized, corresponding region on the second DNA strand of the nucleic acid polymer) for sequencing specific hybridization with labeled probes to generate detectable and identifiable signals.

Figure 1B:
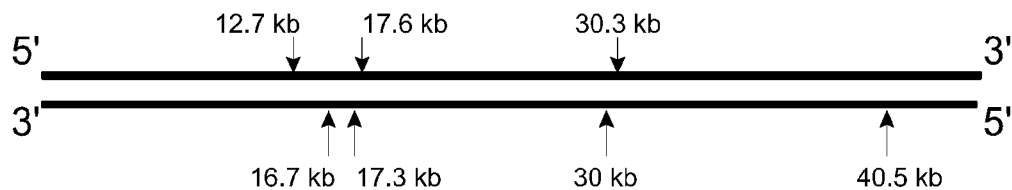
FIG. 1B depicts a schematic view of the claimed flap-labeling methods, including "Flap generation" and "Hybridization of fluorescent sequence specific probe at one site"
Figure 1B:
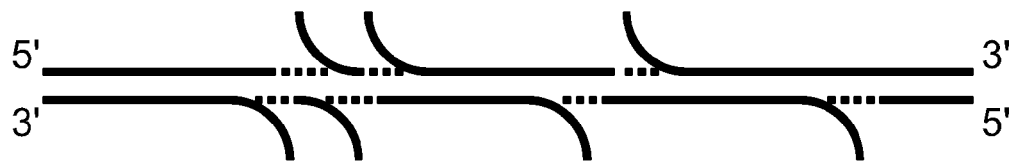
Figure 1B:
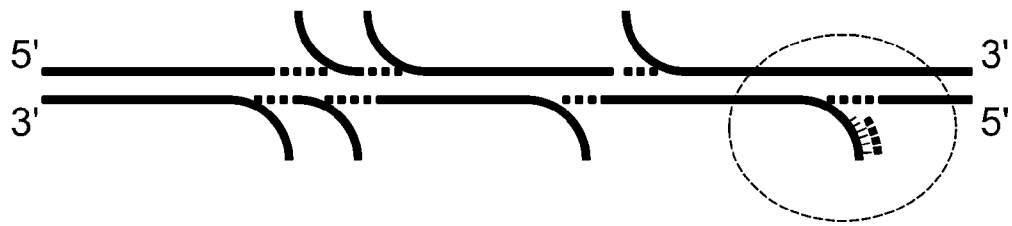
Figure 1B:
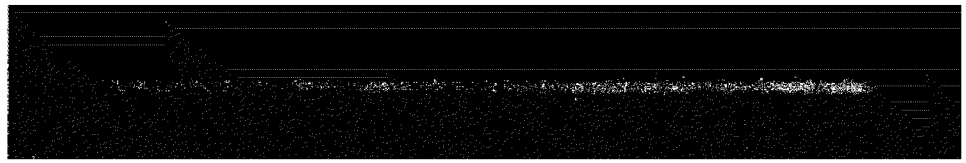

FIG. 1b shows a labeled large genomic DNA being unfolded linearly within a nanochannel. As shown at the bottom of the figure, a fluorescently labeled flap enables the user to visualize the location of the probe within the larger context of the macromolecule. As shown, a nicked-labeled macromolecule may be linearized within a nanochannel. The spatial distance between signals from tags is consistent and can then be quantified, which in turn provides for a unique "barcoding" signature pattern that reflects specific genomic sequence information about the region under analysis. Multiple nicking sites on a lambda dsDNA (48.5 kbp total length) were shown as an example created by a specific enzyme, include but not limited to Nb.BbvCI; Nb.Bsml; Nb.BsrDI; Nb.BtsI; Nt.AlwI; Nt.BbvCI; Nt.BspQI; Nt.BstNBI; Nt.CviPII and the combination digestion of any of above.

A linearized single lambda DNA image is included to show a fluorescently labeled oligonucleotide probe hybridized to an expected nickase created location. Such recorded actual barcodes along long biopolymers are described elsewhere herein as observed barcodes.

By linearizing a macromolecule having labeled flaps, labeled gaps, or both, the user can determine the relative positions of the labels to one another. As described elsewhere herein, such relative distance information is useful in diagnostic applications and in characterizing the nucleic acid polymer.

In some embodiments, the methods further include obtaining sequence information derived from one or more replacement bases incorporated into the first DNA strand of the double-stranded DNA, from one or more probes binding to a flap, or both. This sequence information may be obtained in a variety of ways.

In one example, a labeled probe complementary to a specific base sequence is introduced to the flap, and the user determines whether that sequence-specific probe binds to the flap. This process may be repeated several times, using probes having different sequence specificities, ultimately enabling the user to determine the sequence of bases residing in the flap.

In another example, the sequence information is obtained by determining the sequence of bases that fill-in the gap left behind by the flap. This may be accomplished by labeling one or more of the bases with the same or different labels and assaying the signals emitted by bases as they are incorporated into the gap or after they are incorporated into the gap. In other embodiments, the user may monitor one or more signals evolved from a polymerase that incorporates bases into the gap so as to determine the sequence of the bases.

Determination of sequence information can be performed in free solution or can be performed in nanochannels, so as to allow for high-resolution analysis of a single DNA polymer. A flap could also be excised via an appropriate enzyme and then the excised flap itself could also be sequenced.

The sequence information may be obtained from a single flap, a single gap, or both. In some embodiments, however, the sequence information is obtained from two or more flaps or gaps, thus enabling faster sequencing of a given target. Sequencing information can also be determined by using sequence-specific probes and determining where (and whether) such probes bind to a portion of the nucleic acid polymer.

Figure 4A:
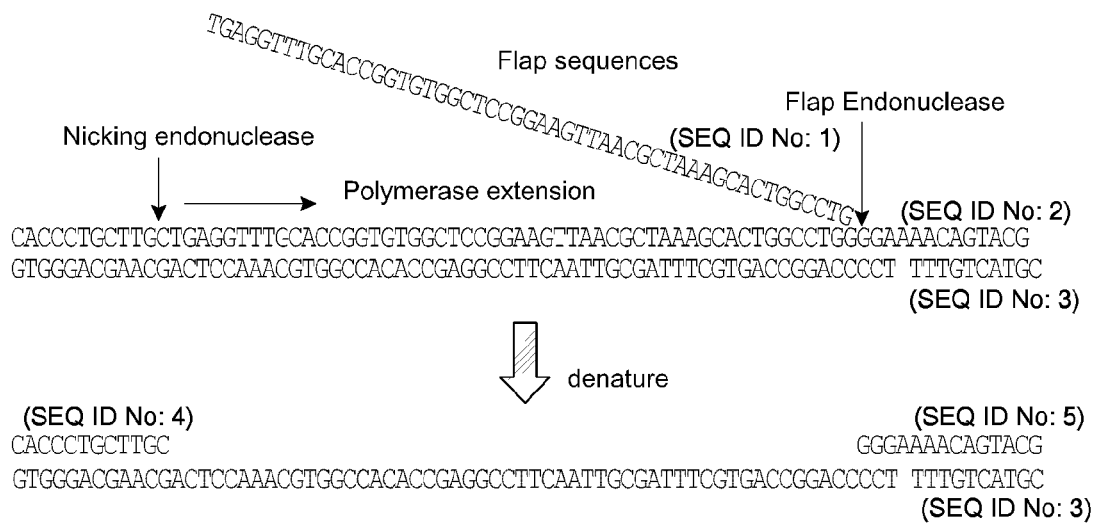
FIG. 4A depicts sequencing along a genomic region, including "then, nick and cut the template by nicking and lap endonuclease to leave a ssDNA gap within dsDNA"
Figure 4B:
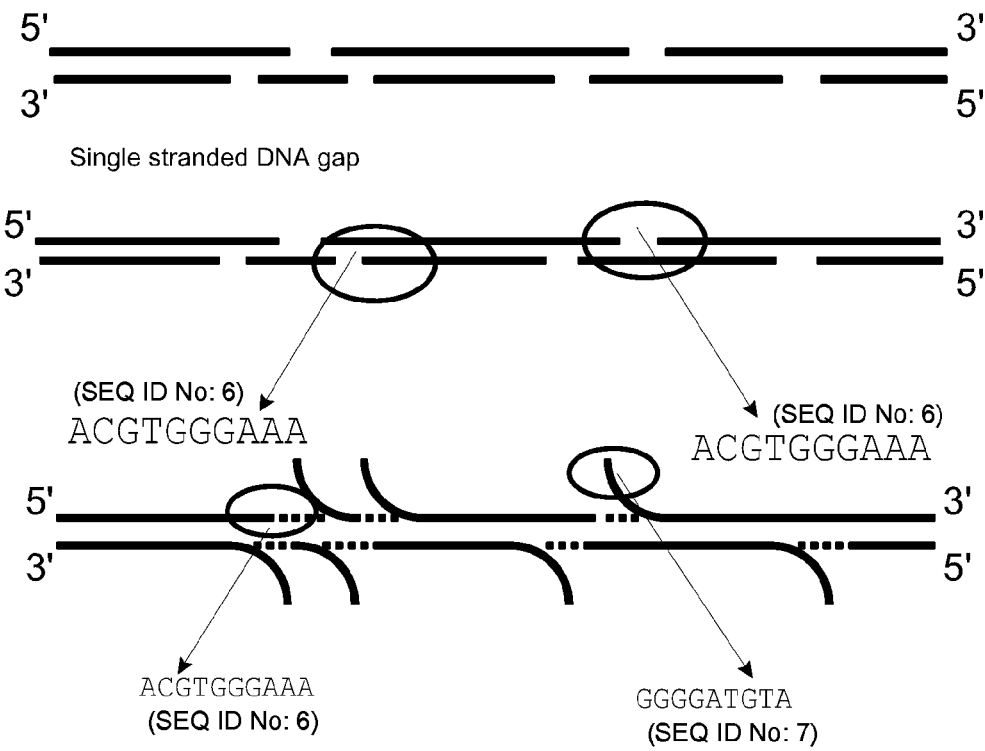
FIG. 4B depicts sequencing along a genomic region, including "single stranded DNA gaps."

FIG. 4 depicts sequencing along a comparatively long genomic region. In that figure, single strand flaps are generated after the "parent" nucleic acid polymer is digested by sequence specific nicking endonuclease and polymerase extension in the first strand of the polymer. This structure can be digested again by a nicking endonuclease and a flap endonuclease, which cuts where flap joins the first strand (shown by arrows), and the resulting dsDNA can be denatured under appropriate conditions so as to generate a single stranded gap that spans the nicking site and the flap endonuclease cutting site. This gap can then be exposed to sequencing reactions using polymerase extension or hybridization and ligation with specific probes and enzymes FIG. 4b depicts a schematic showing multiple nicking sites, single stranded flap sites, and single stranded gap sites created along a long dsDNA. Sequencing reactions are then initiated at one or more nicking, flap sequence sites or single stranded gap sites, with the sequencing effected by polymerase extension or sequencing by hybridization or ligation.

A variety of species can serve as tags for the present methods. A tag can include, for example, a fluorophore, a quantum dot, a dendrimer, a nanowire, a bead, a peptide, a protein, a magnetic bead, a methyl group, a methyl^transferase, a non-cutting restriction enzyme, a zinc-finger protein, an antibody, a transcription factor, a DNA binding protein, a hairpin polyamide, a triplex-forming oligodeoxynucleotide, a peptide nucleic acid, and the like. The methods may include the use of two or more different tags, and a single molecule may accordingly include multiple tags.

The methods also include detecting one or more signals from one or more tags. Such signals can include a fluorescent signal, a chemoluminescent signal, an electromagnetic signal, an electrical signal, a potential difference, and the like. The signal may be related to a physical size difference between two bodies, which may be, for example, the signal evolved when a bead attached to a DNA target is entrapped in a constriction that is smaller in cross-section than is the bead. Fluorescent signals are considered especially suitable, particularly in embodiments where a fluorescent molecule is attached to a base, a probe, or both.

In some embodiments, the signal may derive from energy transferred (e.g., fluorescence energy transfer, "FRET") between a tag on a replacement base and a tag on a probe residing on a flap, by fluorescence resonance energy transfer between two or more tags on a probe residing on a flap, or by any combination thereof.

Figure 2:
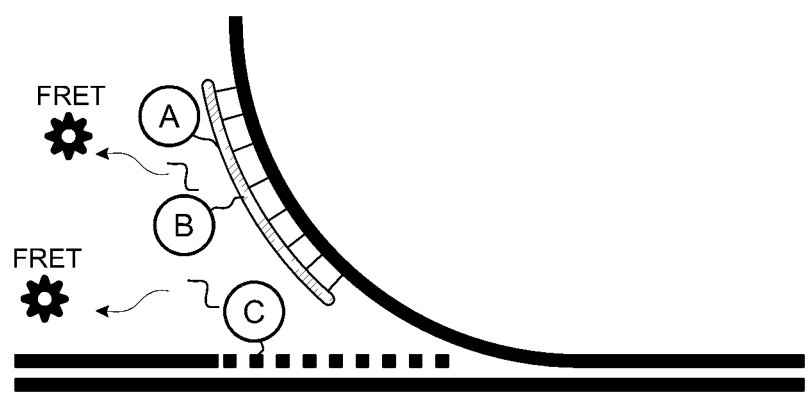
FIG. 2 depicts labeled probes hybridized to a flap generated from a first DNA strand and a label residing in the region of the first strand corresponding to the flap.

FIG. 2 illustrates exemplary positions for labels and probes on nucleic acid polymers prepared according to the claimed invention. That figure depicts probes (shown as A and B) disposed on a flap and a probe (shown as C) along a DNA stranded extended so as to fill-in the gap left behind by the formation and peeling of the flap.

The probes include, for example, organic fluorophore, quantum dot, dendrimer, nanowires, bead, Au beads, paramagnetic beads, magnetic bead, polystyrene bead, polyethylene bead, peptide, protein, haptens, antibodies, antigens, streptavidin, avidin, neutravidin, biotin, nucleotide, oligonucleotide, sequence specific binding factors such as engineered restriction enzymes, methy ^transferases, zinc finger binding proteins, and the like. As shown, more than one probe may be disposed on a flap. In a sample embodiment, a tag (or tags) within a gap are excited by an excitation radiation. The excited gap-tag then transfers energy to a tab disposed on a probe that is itself disposed on the flap.

One or both of the gap- and flap-tags may emit a signal that is detectable by the user. In some embodiments, the gap tag, the first flap tag, or both may excite a second flap tag. In this way, the user may configure a detection system that is highly specific by choosing tags that are excited only by specific wavelengths or types of radiation, thus creating a system in which the tag that is detected by the user is only excited if one or more precursor tags are in proper position. Thus, a co-localization event can be detected (e.g., visualized) by energy transfer between two or more labels, which enhances the specificity of the binding event assay.

The flap region is, in some cases, selected because the flap, gap, or both includes at least a portion of a specific sequence of interest on the double-stranded DNA. Such sequences of interest may include, for example, a sequence known to code for a particular protein or a particular condition.

In some embodiments, the flap, gap, or both, includes at least a portion of the double-stranded DNA that flanks the sequence of interest on the double-stranded DNA. This is useful where, for example, the user seeks to label regions on a DNA that bracket the location of a particular gene or other area of interest so as to highlight that area.

The claimed methods also include at least partially linearizing (e.g., untangling) at least a portion of the double-stranded DNA comprising at least one flap, one gap, or both. The user may also at least partially linearize at least a portion of the double-stranded DNA comprising at least two flaps, two gaps, or any combination thereof. Such linearization may be accomplished, for example, by translocating a DNA through a channel or other structure of such dimensions that the DNA is linearized by way of physical confinement within the channel or other structure.

The user may also, in some embodiments, measure the distance between two flaps, between two or more tags disposed adjacent to two or more flaps, two or more tags disposed within two or more gaps, or any combination thereof. This distance is then suitably correlated to structure, a sequence assembly, a genetic or cytogenetic map, a methylation pattern, a location of a cpG island, an epigenomic pattern, a physiological characteristic, or any combination thereof of the DNA. Because the claimed invention enables investigation of structure and of other epigenomic factors (e.g., methylation patterns, location of cpG islands, and the like), the user can overlay results relating to structure and epigenomic patterns to arrive at a complete genomic picture.

One aspect of the claimed invention is its ability to provide both genomic (sequence) and epigenomic (sequence) information about a nucleic acid or other genetic material. More specifically, the claimed invention allows the user to determine, by way of sequencing, whether a particular gene is present and also, by way of obtaining epigenomic information, the activity of that gene.

In one non-limiting example, a user may obtain genomic information (via the labeling methods described elsewhere herein) about a nucleic acid polymer, such as whether a particular gene is present. The user can then also obtain epigenomic information about the nucleic acid polymer's methylation patterns (which are indicative of the activity of those gene loci located proximate to the methylation) by using, for example, a labeled methyl-binding protein so as to identify the positions of methyls along the nucleic acid polymer. Such methyls may reside on cytosines and within so-called cpG island clusters, which may be correlated to the regulation of functional gene loci. Other binding molecules (such as molecules that bind to transcription factor binding sites and the like) are also suitable for obtaining epigenomic information.

Thus, a user can determine—simultaneously, in some embodiments—the presence of one or more functional genes and, via methyl-based epigenomic information, whether such genes are active. In one example, the user might label the genes' sequence information with label of a first color and label the methylation regions with a label of a second color, thus enabling observation of gene location/sequence and gene activity (i.e., methylation patterns) simultaneously. The epigenomic information may also include locations where transcription enzymes can—or cannot—bind.

The utility of epigenomic information is apparent. As described elsewhere herein, the utility of genomic information is that an oligomer-based probe (or set of probes comprising a barcode) provides "static" information regarding the sequence of the nucleic acid polymer under study. Epigenomic information (e.g., information regarding methylation or transcription factor binding) provides dynamic information about a gene sequence, effectively providing on/off information about the gene. The present invention thus enables simultaneous collection of both genomic and epigenomic information.

As one illustrative, non-limiting example, a user may label locations (i.e., flaps, filled-in gaps, or some combination of the two) on DNA from a first patient, the locations being chosen such that they are up- and down-stream from (i.e., flank) the location of a particular gene, e.g., a breast cancer gene, on the DNA. After linearizing the labeled DNA, the user may compare the distance between these labels to the distance between corresponding labels on a DNA from a control subject known to have a "proper" number of copies of the breast cancer gene. If the distance between the labels for the first patient is greater than the distance between the labels for the control subject, it is then known that the patient has additional or extra copies of the breast cancer gene, and a treatment regimen can be designed accordingly.

The technique can also be used to determine copy number variations between two or more individuals, none of which is a "control" or even copy number variations within a single patient (i.e., by comparing DNA taken from the patient at two different times). In this way, the present methods facilitate rapid analysis and characterization of DNA or other macromolecules from a single subject or from a larger population segment.

The user may also measure the intensity of at least one signal from at least one tag disposed adjacent to a flap, a tag disposed within the gap, or both. The user may then correlate the intensity of the at least one signal to a sequence assembly, a genetic or cytogenetic map, a physiological characteristic, or other features (e.g., epigenomic patterns) described elsewhere herein. This enables the user to develop a complete picture of the pathophysiological state of the source of the nucleic acid polymer.

Figure 5A:
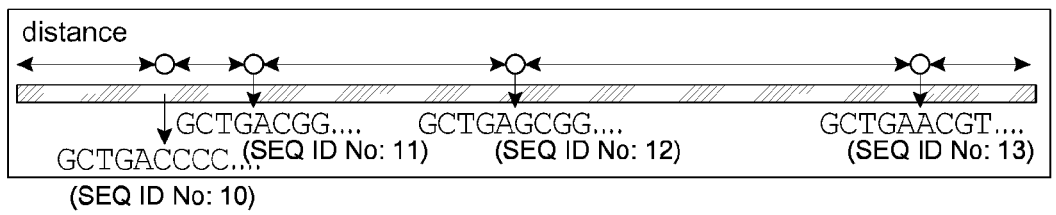
FIG. 5A depicts concurrent parallel sequencing and spatial assembly.
Figure 5B:
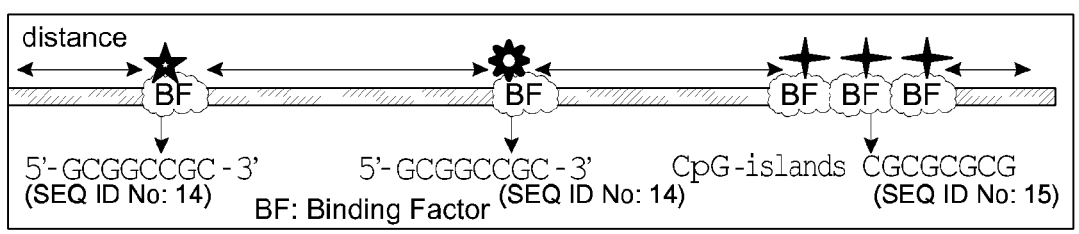
FIG. 5B is a schematic illustration, showing the use of a DNA binding factor (BF), including genetic engineered nonfunctional restriction enzymes that retain only the binding domain of a restriction enzyme but alck the DNA cutting function.
Figure 5C:
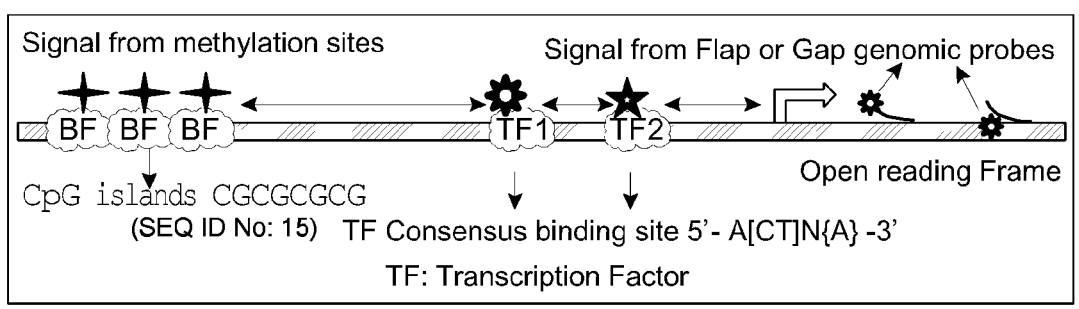
FIG. 5C depicts concurrent parallel sequencing and spatial assembly, including "epigenetic patters overlay with genomic location patterns in real time"

This is shown by non-limiting FIG. 5c. That figure shows, schematically, the use of a labeled binding factor (BF), such as a anti-methyl-antobody or a methyl-binding protein (MBP) to locate one or more epigenomic sites of interest along a genomic region to generate an epigenomic barcode pattern. As shown, the user also—simultaneously, in some cases—uses the disclosed methods to "barcode" the same region (using, e.g., sequence-specific probes) to determine the genomic region's structure. The genomic probes may emit or excite at a different different wavelength or with a signal distinguishable from any labels associated with the epigenomic analysis. In one embodiment, the epigenomic barcodes include (but are not limited to) patterns derived from transcription factor binding sites or siRNA or LincRNA binding sites. This demonstrates the capability of the claimed invention to correlate static genomic sequence and structure information with dynamic regulatory and functional information simultaneously, in real time, and in the same field of view with direct imaging at the single molecule level.

As another non-limiting example, a user may label one or more flaps (or filled-in gaps) corresponding to regions of DNA from a first patient that are within a gene (e.g., breast cancer) of interest. The user then measures the intensity of one or more signals evolved from these labels. The user then measures the intensity of one or more signals evolved from corresponding labels on DNA from a "control" or second subject. If the intensity of the signal(s) from the first patient differs from the intensity of the signal(s) from the control, the user will have some indication that the two subjects have different copy numbers of the gene. Intensity signals may also be correlated to the prevalence of a single base or a particular sequence of bases in a given polymer. The intensity of a signal may also provide information regarding the spatial density of sequences complementary to the probe bearing the label emitting the signal.

Figure 7:
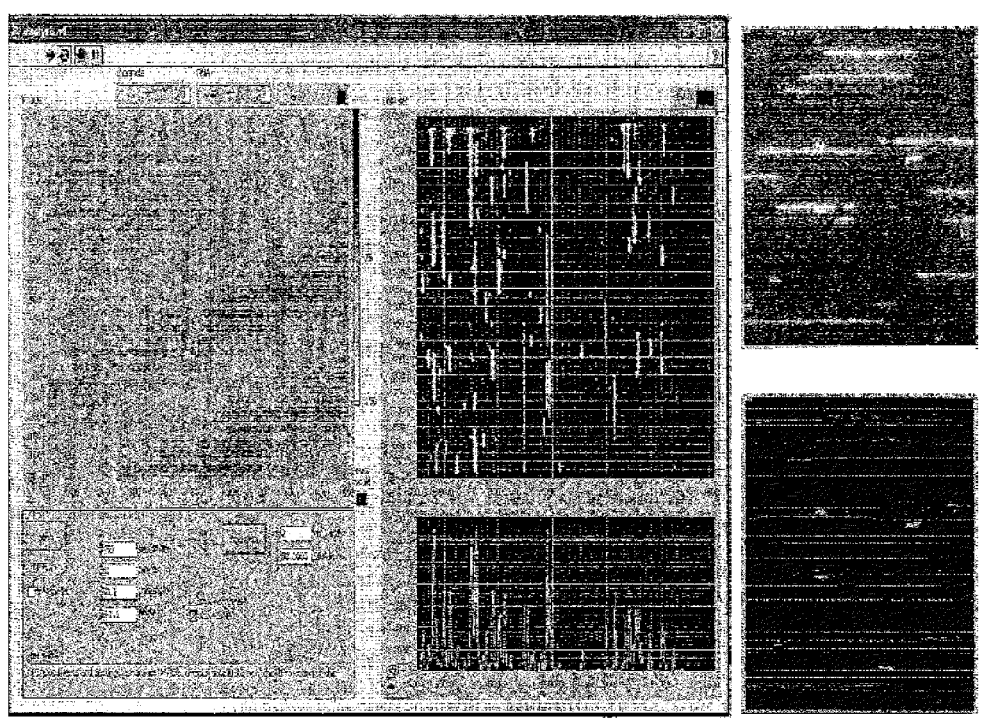
FIG. 7 is a software image of labeled DNA polymers undergoing image analysis.

FIG. 7 illustrates image analysis performed on nucleic acid polymers according to the claimed invention. More specifically, the figure shows "raw" DNA images captured, with end-to-end contour length and intensity information being extracted and measured in real-time. A histogram of the size distribution is shown so as to demonstrate the readings that result from a heterogeneous mixture of DNA.

The claimed invention also provides methods of characterizing multiple DNAs. These methods include labeling, on a first double-stranded DNA, two or more locations (sequence-specific, random, or both) on the first DNA; labeling, on a second double-stranded DNA, the two or more corresponding sequence-specific locations on the second DNA; linearizing at least a portion of the first double-stranded DNA; linearizing at least a portion of the first double-stranded DNA; and comparing the distance between two or more labels on the first, linearized double-stranded DNA to the distance between the corresponding labels on the second, linearized double-stranded DNA.

In some embodiments, the labeling is accomplished—as described elsewhere herein—by nicking a first strand of a double-stranded DNA so as to give rise to (a) flap of the first strand being separated from the double-stranded DNA, and (b) a gap in the first strand of the double-stranded DNA defined by the site of the nicking and the site of the flap's junction with the first strand of the double-stranded DNA.

The methods may further include exposing the flap to a labeled probe complementary to at least a portion of the probe, inserting into the gap one or more labeled bases, or both. As described elsewhere, the labeling is suitably accomplished by exposing the first and second double-stranded DNAs to a non-cutting restriction enzyme, a methyltransferase, a zinc-finger protein, an antibody, a transcription factor, a DNA binding protein, a hairpin polyamide, a triplex-forming oligodeoxynucleotide, a peptide nucleic acid, and the like. The non-cutting restriction enzyme may include a tag. The distance is then suitably correlated to, as described elsewhere herein, a structure, a sequence assembly, a genetic or cytogenetic map, a methylation pattern, a physiological characteristic, a location of a cpG island, an epigenomic pattern, or any combination thereof, of the DNA.

One embodiment of these methods is shown in FIG. 5, which is a schematic illustration showing parallel sequencing and spatial assembly at the same time. Many sequence initiation sites along long genomic region can be created in a sequence motif specific fashion, in this case, GCT-GAxxxx, and the physical locations of these sites are detected and registered on a physical map. Subsequent reads are recorded by a sequencing chemistry, either by sequencing with polymerase extension or hybridization and ligation with specific probes.

In addition to the sequencing reads, the corresponding linear order, and spatial distance and locations of these multiple sequencing reads are recorded and assembled onto a physical map simultaneously. Such a map-based sequencing scheme ultimately provides better assembly accuracy, efficiency and cost reduction over existing methods.

FIG. 5b is a schematic illustration, showing the use of a DNA binding factor (BF), including genetic engineered nonfunctional restriction enzymes that retain only the binding domain of a restriction enzyme but lack the DNA cutting function of such enzymes. DNA methyltransferases that recognize and bind to DNA in a sequence specific fashion are also useful, as are other enzymes, zinc finger proteins, transcription factors bind to DNA in a sequence motif specific, methyl binding proteins or anti-methyl antibodies that bind to methylation specific sites, other DNA associated factor specific (secondary binding) fashion. For example, DNA methyltransferases (MTase) include but are not limited to M.BseCI (methylates adenine at N6 within the 5'-ATCGAT-3' sequence), M.TaqI (methylates adenine at N6 within the 5'-TCGA-3' sequence) and M.HhaI (methylates the first cytosine at C5 within the 5'-GCGC-3' sequence).

In general, this listing of suitably binding bodies includes those bodies that bind (e.g., in a sequence-specific fashion) to double-stranded DNA without also cutting that same dsDNA. In the figure, the various stars represent different labeling tags, such as QD (quantum dots), fluorescent labels, and the like. The spatial distance between these tags and the intensity of these "dots on a string" barcode patterns can be used to study other biological functions such as active transcription sites, ORFs (open reading frames), hypo and hyper-methylated sites, and the like.

In another aspect, the claimed invention provides methods of obtaining structural information from DNA. These methods include labeling, on a first double-stranded DNA, one or more sequence-specific locations on the first DNA. The methods also include labeling, on a second double-stranded DNA, the corresponding one or more sequence-specific locations on the second double-stranded DNA; linearizing at least a portion of the first double-stranded DNA, linearizing at least a portion of the first double-stranded DNA; and comparing the intensity of a signal of the at least one label of the first, linearized double-stranded DNA to the intensity of the signal of the at least one label of the second, linearized double-stranded DNA.

As described elsewhere herein, the labeling is suitably accomplished by nicking a first strand of a double-stranded DNA so as to give rise to (a) flap of the first strand being separated from the double-stranded DNA, and (b) a gap in the first strand of the double-stranded DNA corresponding to the flap, the gap defined by the site of the nicking and the site of the flap's junction with the first strand of the double-stranded DNA. The flap is suitably exposed to a labeled probe complementary to at least a portion of the probe, inserting into the gap one or more labeled bases, or both, so as to extend the first strand along the corresponding region of the second DNA strand. The signal intensities are then correlated to at least one physiological characteristic of a donor of the nucleic acid polymer. The intensity may also be related to a structural characteristic of the nucleic acid polymer, an epigenomic pattern, or both.

The present invention provides the user the ability to obtain and analyze both structural and epgenomic information from a given polymer. As described elsewhere herein, the claimed invention provides a "barcoding" technique by which a region of nucleic acid polymer is given a unique signature. This barcode can be applied (as described elsewhere herein) so as to provide information regarding structure (by way of, e.g., labels with sequence specific motifs, first barcodes) and epigenomic patterns (by way of labels specific to an epigenomic indicator, such as a methylation site, a cpG island, and the like, second barcodes). By utilizing information gleaned from both first and second barcodes, the user can obtain structural and epigenomic information regarding a given nucleic acid polymer.

Also provided are methods of obtaining structural information from a macromolecule, such as double-stranded DNA. These methods include translocating a macromolecule comprising at least one flap extending therefrom along a channel having at least one constriction disposed therein; and detecting at least one signal corresponding to the passage of the at least one flap of the macromolecule through the at least one constriction of the channel. In some embodiments, the flap is labeled, in others, it is not, and the signal is related to the passage of the "bare" flap past the constriction.

Suitable channels are known in the art, e.g., the channels described in U.S. application Ser. No. 10/484,293, which is incorporated herein in its entirety. In some embodiments, the flap—or a region of the macromolecule adjacent to the flap—comprises a label. In some embodiments, a label is disposed within the filled-in gap left when the flap was formed, as described elsewhere herein.

The signal is suitably an optical signal, an electrical signal, an electromagnetic signal, or even some combination thereof. The signal may be related to the passage of the flap through the constriction, or may be related to the passage of the label through the constriction. The flap may be translocated through a constriction more than once.

Exemplary, non-limiting embodiments of these methods are shown in FIG. 8. That figure first (FIG. 8a) depicts a system for obtaining labeled barcode information from a nucleic acid polymer, utilizing both optical and non-optical detection methods.

As shown, a labeled long nucleic acid molecule is shown stretched and linearized within a nanochannel having one or more narrow constrictive points (known as nanogates or nanonozzles; see U.S. application Ser. No. 12/374,141, the entirety of which is incorporated herein by reference).

In some embodiments, DNA movement and current measurement are controlled by an electrical circuit in connection with fluidic devices and external reservoirs. Optical images of the barcodes patterns and non-optical recording of the labels (i.e., electrical recording of physical "bumps" along the uniform polymers) are shown in, are schematically shown in FIG. 8b and FIG. 8c. The optical and non-optical results may be correlated or compared against one another for better data accuracy.

FIG. 8d depicts a nanogate-comprising fluidic device. Shown here is a series of "flaps" generated by methods previously described, which flaps may include additional labeling tags. The flaps, their tags, or both are detected directly during passage through the nanogates, during which the flaps, tags, or both generate detectable electronic signals such as an ionic current signatures reflecting the target genomic region. Labeled bases may—as described elsewhere herein—also be present in the nucleic acid polymer in the region vacated by the flap. Such bases may also be detected as they pass by a nanogate.

Also provided are methods of obtaining structural information from a macromolecule. These methods include labeling at least a portion of a macromolecule; immobilizing the macromolecule; disposing at least a portion of the macromolecule within a channel such that at least a portion of the macromolecule is linearized within the channel; and detecting at least one signal related to the labeled portion of the macromolecule.

Figure 9:
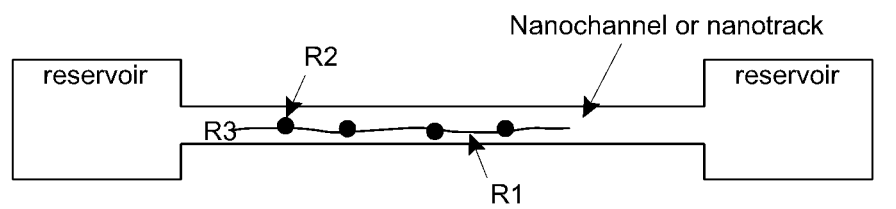
FIG. 9 depicts a labeled nucleic acid polymer linearized within a nanochannel or nanotrack.

FIG. 9 depicts a tethered nucleic acid at one end or both ends inside a nanochannel or nanotrack on the surface of a substrate for sequence imaging analysis. As shown in the figure, a region of the nucleic acid polymer is modified to enable tethering, the nucleic acid polymer having a sequence (R2) that is labeled or other wise being analyzed at multiple locations.

As a non-limiting example, R2 may be known to reside within a gene for a particular disease, and the presence of multiple R2 sequences within the polymer may demonstrate an abnormal (or normal) number of copies of that sequence. The polymer may be translocated along the channel from one reservoir to another, and may be stopped or immobilized at any point along its translocation path.

Figure 10A:
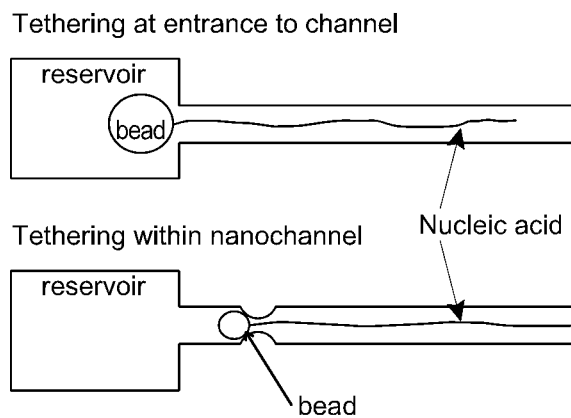
FIG. 10A depicts nucleic acid polymers immobilized adjacent to or within nanochannels, by various means, including a macromolecule bound to a bead.

The immobilization may be accomplished in a number of ways. In one embodiment, as shown in FIG. 10a, the macromolecule is bound to at least one bead, the molecule being immobilized by the at least one bead being caught by a constriction smaller in cross-section than the bead. Immobilization may also be accomplished by chemically tethering the macromolecule to a surface, by magnetically immobilizing the macromolecule, by optically trapping the macromolecule, or any combination thereof.

In embodiments including a bead, the bead is chosen such that its effective diameter is larger than at least one of the cross-sectional dimensions of the nanochannel. As the modified nucleic molecule is flowed into the nanochannel, its flow is impeded because the modifying bead is larger than at least a portion of the nanochannel. The unmodified portions of the nucleic acid molecule can then be linearized and are available for sequence analysis. The bead can be polymeric, magnetic, semi-conducting, dielectric, metallic or any combination thereof and modification of the nucleic acid molecule can be based on a covalent bond or non-covalent interaction including protein interactions and can involve an intermediary linkage. In all modes of tethering or immobilization, an applied flow or gradient field may be modulated so as to enable or disengage the tethering.

The modifying species for tethering can be chosen such that the nature of binding of the nucleic acid molecule within the nanochannel is magnetic, electrical, optical, chemical, frictional, flow-based, physical obstruction or any combination thereof.

Figure 10B:
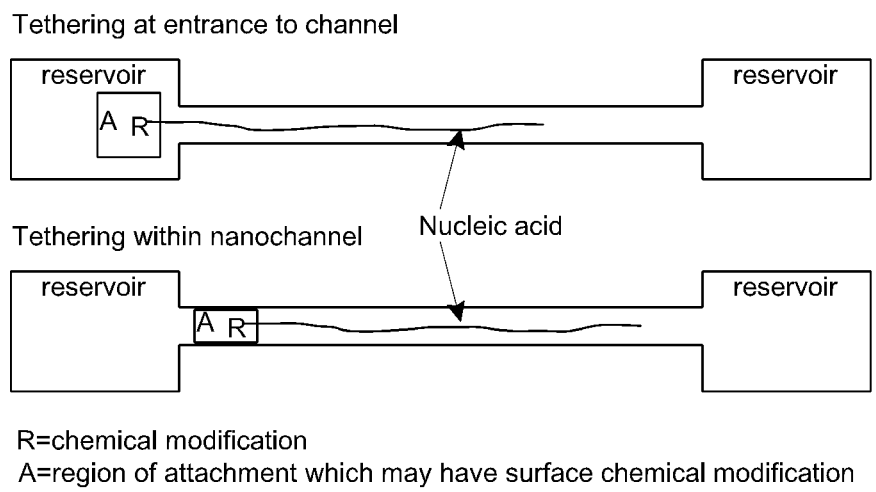
FIG. 10B depicts nucleic acid polymers immobilized adjacent to or within nanochannels, including showing a nucleic acid molecule is chemically modified at or near one end.

In another embodiment, a nucleic acid molecule is chemically modified at or near one end of the molecule, as shown in non-limiting FIG. 10b. The chemical modification is chosen such that a covalent or non-covalent interaction occurs between the modifying species and the nanochannel material of sufficient strength to tether the nucleic acid molecule and prevent its flow through the nanochannel.

Examples of chemical modifiers include thiol groups, silane groups, carboxy groups, amine groups, alkyl chains, phosphate groups, photocleavable groups, proteins, biotin, amino acid residues, metallic groups, or any combination thereof. In some cases, the nanochannel surface may include some chemical modification to facilitate the interaction with the modifying species.

In another embodiment, a nucleic acid molecule is magnetically modified at or near one end of the molecule, as shown in FIG. 11a. The magnetic modification can be a magnetic bead, paramagnetic particle, superparamagnetic particle, or other moiety capable of sustaining a magnetic dipole for the duration of the sequence analysis. In such a case, the magnetic force can be integrated into or near the nanochannel device or, alternatively, can be the consequence of an externally applied magnetic field, also as shown in FIG. 11a.

In another embodiment, a nucleic acid is modified at or near one end of the molecule with a particle or moiety capable of experiencing a dielectric force gradient in the presence of optical tweezers. This is shown in non-limiting FIG. 11b.

As shown, optical tweezers are used to trap the particle within confines of the beam when the particle is flowing through the nanochannel thus allowing the attached nucleic acid molecule to be linearized within the nanochannel. The optical tweezers can be used to move a target as well as immobilize it.

In another embodiment, multiple forces are employed to immobilize or tether the DNA. For example, an opposing fluid flow and an electric field can be employed concurrently to keep the molecule stretched and stationary within the area of analysis.

Linearization is suitably accomplished by a channel that is suitably sized so as to effect linearization of the macromolecule, suitably by physical-entropic confinement.

Also provided are analysis systems. Systems according to the claimed invention include a substrate comprising at least one channel having a width in the range of from about 1 to about 500 nanometers; the substrate comprising at least one immobilization region. The channels suitably have a width in the range of from about 10 to about 200 nm, or from about 20 to about 100 nm, or even about 50 nm. The channels' depth may be in the same range, although the width and depth of a particular channel need not be the same. Channels can be of virtually any length, from 10 nm up to centimeters. Such channels suitably have a length in the millimeter range, although the optimal length for a given application will be apparent to the user of ordinary skill in the art.

The immobilization region is capable of immobilizing a macromolecule. Macromolecules may include one or more modifications, which can include flaps, beads, dielectric modifications, magnetic particles, and the like. The systems and macromolecular modifications may be chosen in concert and on the basis of their affinity for one another. Exemplary immobilization regions include magnetic regions, chemically active regions, constrictions, and the like, as shown in FIG. 10 and FIG. 11.

In some embodiments, the polymer is immobilized, and a gradient is applied so as to disposed at least a portion of the polymer in the channel, as shown in FIG. 10 and FIG. 11. In this way, a polymer—which can be labeled, as described elsewhere herein—may be linearized and, by virtue of its confinement within the channel, may remain in linear form.

While not shown in the figures, the present invention also include embodiments in which a labeled polymer is immobilized or tethered and then linearized by application of a gradient (pressure, electrical, and the like) in order that one or more labels (or flaps) disposed on the polymer can be detected and correlated to a characteristic of the polymer. The polymer can be maintained in a linear form by continued application of the gradient or by being adhered to a substrate once it has been linearized by the gradient (i.e., the polymer is linearized and then adhered down the substrate in its linearized form).

Also provided are methods of characterizing a nucleic acid polymer. These methods include labeling one or more regions of a nucleic acid polymer with one or more sequence-specific motif labels; correlating one or more signals from one or more of the sequence-specific motif labels to the position of the one or more sequence-specific motif labels of the nucleic acid polymer; sequencing one or more segments of the nucleic acid polymer, the one or more segments including one or more of the sequence specific motif labels of the nucleic acid polymer; and comparing one or more signals of one or more sequenced segments to one or more corresponding signals of the labeled nucleic acid polymer so as to develop the relative locations within the nucleic acid polymer, of two of more sequenced segments.

The labeling aspect of the claimed methods is suitably accomplished by labeling methods described elsewhere herein, i.e., forming a flap in the nucleic acid polymer and labeling the flap, the region vacated by the flap, or any combination thereof. Suitable labels and tags are described elsewhere herein.

Correlating suitably entails linearizing at least one labeled portion of the nucleic acid polymer. The linearization may be accomplished by linearizing the labeled portion of the polymer in a suitably sized nanochannel, by applying a gradient (fluid, electrical, for example) to the polymer, and the like. In other embodiments, the polymer is tethered or otherwise immobilized and linearized by application of a gradient (pressure, electrical, and the like). Segments may be generated by random or sequence-specific cleaving of the nucleic acid polymer.

The correlating may include, for example, determining the distance between two or more labels, comparing the intensity of signals evolved from two or more labels, and the like. Sequencing of the segments of the polymer—known, in some instances, as "contigs", may be accomplished by a variety of techniques known in the art. These techniques include, for example, Sanger sequencing, Maxam-Gilbert sequencing, dye terminator sequencing, in vitro clonal amplification, sequencing by hybridization, and the like. Segments are suitably up to 30 kb or even 50 kb in length, but are suitably in the kb length range.

Comparing the signal or signals of a labeled segment to the corresponding signal of the labeled nucleic acid polymer is accomplished, for example, by aligning one or more labeled, sequenced segments against the labeled nucleic acid polymer such that a sequence-specific motif label of the labeled, sequenced segment is placed in register with the corresponding sequence-specific motif label of the labeled nucleic acid polymer. This effectively allows the user to utilize the labels on the segments as "barcodes" that allow for identification of individual segments. Thus, by matching a barcoded contig against the corresponding barcode on the "parent" nucleic acid polymer, the user may determine the position (and orientation) of the barcoded contig within the "parent" nucleic acid polymer.

In this way, by aligning one or more signals from labels on the segment with the corresponding labels on the "mother" polymer, the user can determine the proper alignment of the segment. By repeating this process for multiple segments, the user can then determine the proper order—and orientation—of the segments, allowing for massively parallel sequencing of nucleic acid polymers.

This process is further depicted in FIG. 6, which depicts the claimed methods of obtaining genome scaffolding (e.g., sequence) assembly information from a nucleic acid polymer.

As shown in the figure, the user extracts comparatively long genomic DNA molecules from a polymer (from 1 kb up to 100 mb or more) and labels the molecules, e.g., according to the labeling methods described elsewhere herein so as to give rise to create sequence specific signals that are detected and recorded along the linearized long polymers to generate a signature "observed barcode" (shown as "Raw Images of OBSERVED BARCODE") that represents particular regions of the molecule genome; the molecules can represent a genome. The observed barcodes from individual molecules can then be assembled into comparatively long scaffolds, which scaffolds can be up to the size of an intact genome.

Discrete segments ("contigs", in some embodiments; from about 5 to about 30 kb) may be computationally assembled based on partial overlapping short base reads generated by current sequencing sequencing technology. Such contigs can be random or be generated on the basis of sequence specificity. As shown in FIG. 6, a genome may be fragmented into contigs of 50 bp up to 1000 bp, for example. The user can then generate many (millions) of short reads, of about 35 to about 850 bps.

One or more of the contigs is suitably labeled with a sequence specific motif (such as a Nb.BbvCI site, GCT-GAGG) identical to the sequence specific motif used to label the "parent" nucleic acid polymer to generate a series of barcodes. Where the contigs are virtually labeled (i.e., via computer), the barcodes are considered in silico barcodes.

The user then aligns the barcodes of the contigs (segments) against the corresponding, observed barcodes of the experimentally constructed scaffolds, which alignment then provides the user with the physical locations of the contigs within the scaffold, along with the proper orientation of a contig within the scaffold. This in turn yields information about the scaffold (and the corresponding genome), such as copy numbers of sequences within the scaffold, structural information (e.g., translation), and the like. Thus, individual contigs are mapped precisely onto the genome so as to generate true, accurate genomic sequencing information of a specific polymer under analysis.

These methods have numerous advantages over existing sequencing techniques, including the ability to provide information regarding copy number and the ability to place contigs in the proper position/order relative to one another. This in turn provides true sequencing information; without the barcoding techniques described herein, the linear order of contigs along the analyzed genome would be unknown, especially if there is no prior reference database to compare against to (de novo sequencing). Due to the high complexity of large genomes having copy number variations (CNVs) and structural variations (SVs), independent assembly directly from random shorter reads, especially for de novo sequencing or highly scrambled cancer genome, has become increasingly difficult and prone to errors.

As one non-limiting example, a first segment (of known sequence) might include barcodes A, B, and C, each of which barcodes correspond to the position of a sequence-specific label on the segment, the intensity of the sequence-specific label, or both. The labeled segment thus presents a unique profile based on the A, B, and C barcodes. A second labeled segment (of known sequence) may include barcodes C, D, and E. By aligning the first and second segments against the "mother" polymer from which the segments were cleaved, the user can determine that the two segments overlap at barcode C and—by combining the sequences of the two segments (without double-counting the sequence corresponding to barcode C)—can determine the sequence of the "mother" polymer from which the two segments were derived. By scaling this process up to address multiple segments simultaneously, the present methods thus enable determination of sequence information for long nucleic acid polymers.

Figure 3A:
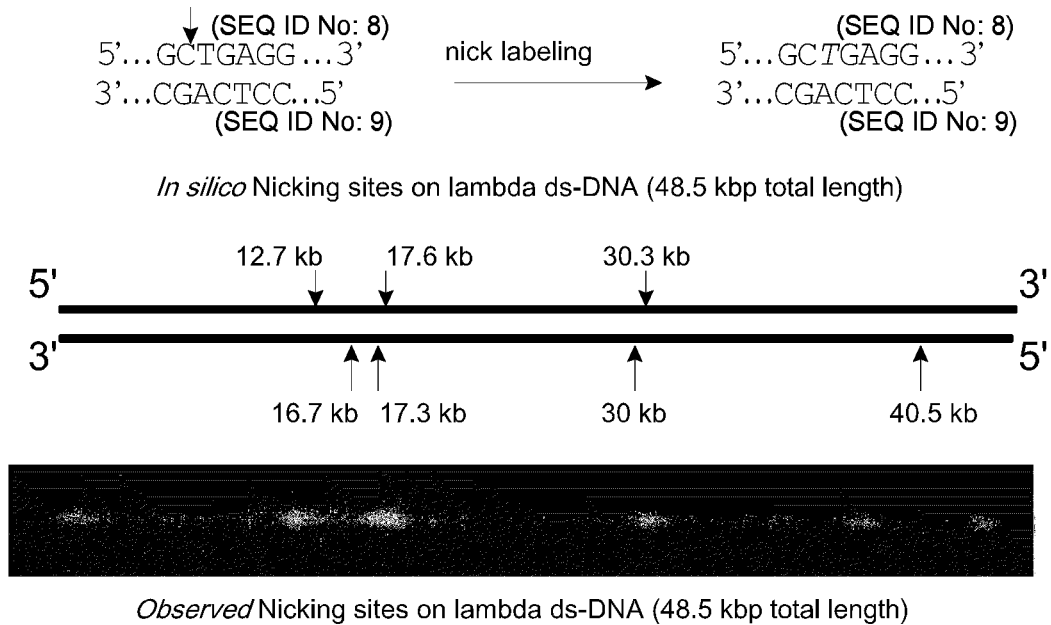
FIG. 3A depicts an alternative embodiment of placing DNA "barcodes" on polynucleic acids, including "in silico Nicking sites on lambda ds-DNA (48.5 kbp total length)" and "Observed Nicking sites on lambda ds-DNA (48.5 kpb total length)"

One similar embodiment is shown in FIG. 3. This figure illustrates an example using Lambda DNA, predicted nicking sites by the nickase Nb.BbvC I are shown in sequence motif and indicated by arrows along the long DNA molecule. The nicking sites are labeled with fluorescent (Alexa)

nucleotides T that are incorporated at the nicking sites (shown in green color), as the native T base is displaced and replaced.

Figure 3B:
FIG. 3B depicts an alternative embodiment of placing DNA "barcodes" on polynucleic acids, including "similar barcode results shown on linearized human BAC clone DNAs with complete stretching (~170 Kb)"

In this model system, the observed signature "barcode" patterns of the labeling agree with the predicted sequence motif map of the genome generated with nicking enzyme digestion in silico, designated here as in silico BARCODE, based on 100% stretched lambda DNA in low salt conditions within 80 nm by 80 nm wide channels, as shown by FIG. 3b. Similar barcode results shown on linearized human BAC clone DNAs with complete stretching (~170 Kbp); over 17 labeled sites (in fluorescent color) are also shown.

ADDITIONAL EXAMPLES AND EMBODIMENTS

Additional Embodiments

As described elsewhere herein, the claimed invention provides, inter alia, methods relating to DNA mapping and sequencing, including methods for making long genomic DNA, methods of sequence specific tagging and a DNA barcoding strategy based on direct imaging of individual DNA molecules and localization of multiple sequence motifs or polymorphic sites on a single DNA molecule inside the nanochannel (<500 nm in diameter). The methods also provide continuous base by base sequencing information, within the context of the DNA map. Compared with prior methods, the claimed method of DNA mapping provides improved labeling efficiency, more stable labeling, high sensitivity and better resolution; our method of DNA sequencing provide base reads in the long template context, easy to assemble and information not available from other sequencing technologies, such as haplotype, and structural variations.

In DNA mapping applications, individual genomic DNA molecules or long-range PCR fragments are labeled with fluorescent dyes at specific sequence motifs. The labeled DNA molecules are stretched into linear form inside nanochannels (described elsewhere herein) and are imaged using fluorescence microscopy. By determining the positions and, in some cases, the colors of the fluorescent labels with respect to the DNA backbone, the distribution of the sequence motifs can be established with accuracy, akin to barcode on a package. This DNA barcoding method is applied to the identification of lambda phage DNA molecules and to human bac-clones.

One embodiment utilizing nicks at specific sequence sites on dsDNA comprises the steps of: a) nicking one strand of a long (e.g., more than 2 kb) double stranded genomic DNA molecule with one or more nicking endonucleases to introduce nicks at specific sequence motifs; b) incorporating fluorescent dye-labeled nucleotides at the nicks with a DNA polymerase; c) stretching the labeled DNA molecule into linear form inside nanochannels, the molecules either flowing through the channels or a portion of the molecule being immobilized such that one end of the DNA is then disposed within the channel; d) determining the positions of the fluorescent labels with respect to the DNA backbone using fluorescence microscopy to obtain a map or barcode of the DNA.

Another embodiment with flap sequences at sequence specific nicking sites comprises the steps of: a) nicking one strand of a long (>2 Kb) double stranded genomic DNA molecule with a nicking endonucleases to introduce nicks at specific sequence motifs; b) incorporating fluorescent dye-labeled nucleotides or none fluorescent dye-labeled nucleotides at the nicks with a DNA polymerase, displacing the downstream strand to generate a flap sequences; c) labeling the flap sequences by polymerase incorporation of labeled nucleotides; or direct hybridization of a fluorescent probe; or ligation of the fluorescent probes with ligases; d) stretching the labeled DNA molecule into linear form as described elsewhere herein; e) determining the positions of the fluorescent labels with respect to the DNA backbone using fluorescence microscopy so as to obtain a map or barcode of the DNA.

Another embodiment utilizing a ssDNA gap at sequence specific nicking sites comprises the steps of: a) nicking one strand of a long (>2 Kb) double stranded genomic DNA molecule with a nicking endonucleases to introduce nicks at specific sequence motifs; b) incorporating fluorescent dye-labeled nucleotide probes or non-fluorescent dye-labeled nucleotides at the nicks with a DNA polymerase, displacing downstream strand to generate one or more flap sequences; c) employing a nicking endonuclease to nick the newly extended strand and cut the newly formed flap sequences with flap endonucleases. The detached ssDNA can be removed by, for example, increasing the temperature so as to release their bonds. d) labeling the ssDNA gap (evolved by the nicking and subsequent formation of the flaps) via incorporation of labeled nucleotides; or direct hybridization of the fluorescent probes; or ligation of the fluorescent probes with ligases. e) stretching the labeled DNA molecule into linear form as described elsewhere herein; f) determining the positions of the fluorescent labels with respect to the DNA backbone using fluorescence microscopy to obtain a map or barcode of the DNA.

In other DNA sequencing applications, individual genomic DNA molecules or long-range PCR fragments are labeled with fluorescent dyes at specific sequence motifs. The labeled DNA molecules are then linearized within nanochannels and are then imaged using fluorescence microscopy. By determining the positions and colors of the fluorescent labels with respect to the DNA backbone, the distribution of the sequence motifs can be established with accuracy, in a manner similar to reading a barcode. Single or multiple bases information were obtained in the context of the DNA map.

One embodiment of this sequencing method applicable to genomic DNA comprises the steps of: a) nicking one strand of a long (>2 Kb) double stranded genomic DNA molecule with a nicking endonucleases to introduce nicks at specific sequence motifs; b) tagging the nicking sites with fluorescent dye molecules through nick-incorporation; flap labeling, ssDNA gap labeling, or some combination thereof; c) stretching the labeled DNA molecule into linear form as described elsewhere herein; d) determining the positions of the fluorescent labels with respect to the DNA backbone using fluorescence microscopy to obtain a map or barcode of the DNA; e) using the nicking sites as the initialization points of sequencing reactions. Different DNA structures including but not limited to the following, are useful in DNA sequencing.

In one sequencing embodiment, a polymerase incorporates fluorescent nucleotides at the 3' end of the nicking sites, sequentially detecting the incorporated labels at each nicking site to obtain the sequence information. This process is repeated/cycled to sequentially obtain "reads" on many bases.

In another embodiment, a sequencing primer is hybridized to a flap sequence and is extended with a polymerase to incorporate a fluorescent nucleotide. By reading the colors of these various incorporated fluorescent nucleotides, sequence information is then inferred. This process is repeated/cycled to obtain many base reads sequentially.

In another embodiment, one short fluorescent oligonucleotide is directly hybridized to the flap sequences, the sequence information can be inferred from the presence of the hybridized oligos. This process is cycled/repeated to obtain many base reads sequentially.

In another embodiment, two short oligonucleotides are hybridized to flap sequences next to each other and are then ligated together with, e.g., ligases, The sequence information can be inferred from the ligation products. This process is repeated/cycled to obtain many base reads sequentially.

In another embodiment, one short fluorescent oligonucleotide is directly hybridized next to the 3' end of the nicking sites and ligated. The sequence information is then inferred from the presence of the ligated oligonucleotides. This process is repeated/cycled to obtain many base read sequentially.

The methods may be performed in conjunction with nanochannel arrays. Such arrays suitably have a plurality of channels in the material of the surface, the channels having a trench width of less than about 500 nanometers and a trench depth of less than 500 nanometers. At least some of the channels are suitably surmounted by sealing material to render such channels at least substantially enclosed.

In some embodiments, the claimed invention includes cartridges or other modular devices. Such cartridges may include, for example, a including a nanofluidic chip in accordance with this invention are also disclosed herein. Such cartridges are capable of being inserted into, used and removed. Cartridges useful with analytical systems other than the systems of the present invention are also within the scope of the present invention.

Nanochannels, in some embodiments, are capable of transporting a macromolecule across their length. Devices of the claimed invention may include one or more components useful in effecting macromolecular transport, which transport may be effected by pressure or vacuum gradients across a channel, electroδsmosis, and electrokinesis.

The surface material of the nanochannels can be formed from almost any substrate material, such as a conductive material, a semiconductor material, or a non-conductive material. Examples of conductive materials include metals such as aluminum, gold, silver, and chromium. Examples of semiconductive materials include doped silicon dioxide and gallium arsenide. Examples of non-conductive materials include fused silica, silicon dioxide, silicon nitride, glass, ceramics, and synthetic polymers. The foregoing is exemplary only.

In some embodiments, a nucleic acid molecule is modified at or near one end and is then disposed into a nanochannel or nanotrack (a region defined by borders that restrain fluid passage, such as hydrophobic borders). The modification suitably permits tethering of the nucleic acid at the entrance of the nanochannel or within the nanochannel. The nucleic acid is then constrained to adopt a linearized form due to the nanochannel The nucleic acid is suitably DNA or RNA, e.g., dsDNA. The nanochannel is preferably <500 nm, more preferably <300 nm and most preferably <150 nm with a length capable of accommodating a linearized nucleic acid with more than 2000 bases.

The following embodiments also apply to nanotracks, which are linear regions defined on chemically or topologically predefined surface patterns.

Fluids that can be analyzed by the system includes fluids from a mammal (e.g., DNA, cells, blood, biopsy tissues), synthetic macromolecules such as polymers, and materials found in nature (e.g., materials derived from plants, animals, and other life forms). Such fluids can be managed, loaded, and injected using automated or manual loading apparatus of the present invention.

EXAMPLES

Example 1

Generating Single Stranded DNA Flaps on Double Stranded DNA Molecules

Genomic DNA samples were diluted to 50 ng for use in the nicking reaction. 1O uL of Lambda DNA (50 ng/uL) were added to a 0.2 mL PCR centrifuge tube followed by 2 uL of 1O× NE Buffer #2 and 3 uL of nicking endonucleases, including but not limited to Nb.BbvCI; Nb.Bsml; Nb.BsrDI; Nb.BtsI; Nt.AlwI; Nt.BbvCI; Nt.BspQI; Nt.BstNBI; Nt.CviPII. The mixture was incubated at 37 degrees C. for one hour.

After the nicking reaction completes, the experiment proceeded with limited polymerase extension at the nicking sites to displace the 3' down stream strand and form a single stranded flap. The flap generation reaction mix consisted of 15 µl of nicking product and 5 µl of incorporation mix containing 2 µl of 1O× buffer, 0.5 µl of polymerase including but not limited to vent(exon-), Bst and Phi29 polymerase and 1 µl nucleotides at various concentration from IuM to ImM. The flap generation reaction mixture was incubated at 55 degrees. The length of the flap was controlled by the incubation time, the polymerases employed and the amount of nucleotides used.

Example 2

Generating Single Stranded DNA Gaps on Double Stranded DNA Molecules

After flap generation, the original nicking endounuclease was used to nick the filled double stranded DNA and Flap endonulceases including but not limited to FEN1 was used to cut the flap sequences. By increasing the temperature, the nicked single stranded DNA molecules were removed from the double stranded DNA molecules to generate a single stranded DNA gap on double stranded DNA molecules.

Example 3

Generating Long Single Stranded DNA Molecules

After the nicking reaction completes, the experiment proceeded with complete polymerase extension including but not limited to Phi29, Bst polymerase at the nicking sites to displace the 3' down stream strand and generate single stranded DNA molecules.

Example 4

The Method of Fluorescently Labeling Sequence Specific Nicks on Double Stranded DNA Molecules Genomic DNA samples were diluted to 50 ng for use in the nicking reaction. 1O uL of Lambda DNA (50 ng/uL) were added to a 0.2 mL PCR centrifuge tube followed by 2 uL of 1O× NE Buffer #2 (New England BioLabs, www.neb.com), and 3 uL of nicking endonucleases, including but not limited to Nb.BbvCI; Nb.Bsml; Nb.BsrDI;

Nb.BtsI; Nt.AlwI; Nt.BbvCI; Nt.BspQI; Nt.BstNBI; Nt.CviPII. The mixture was incubated at 37 degrees C. for one hour.

After the nicking reaction completes, the experiment proceeds with polymerase extension to incorporate dye nucleotides onto the nicking sites. In one embodiment, a single fluorescent nucleotide terminator was incorporated. In another embodiment, multiple fluorescent nucleotides were incorporated.

The incorporation mix consisted of 15 μl of nicking product and 5 μl of incorporation mix containing 2 μl of 10× buffer, 0.5 μl of polymerase including but not limited to vent(exon-), 1 μl fluorescent dye nucleotides or nucleotide terminators including but not limited to cy3, alexa labeled nucleotides. The incorporation mixture was incubated at 55 degrees C. for about 30 minutes.

Example 5

The Method of Sequence Specific Labeling Single Stranded DNA Flaps on Double Stranded DNA Molecules Once the flap sequence was generated, the flap can be labeled with fluorescent dye molecules including but not limited to the following methods, hybridization of probe, incorporation of fluorescent nucleotide with polymerase and ligation of fluorescent probes.

Example 6

The Method of Sequence Specific Labeling Single Stranded DNA Gaps on Double Stranded DNA Molecules A nanofluidic chip having a width, depth, or both of 500 nm or less is filled using capillary action with a buffer solution containing stained genomic DNA to draw the DNA macromolecules into the channels with an electric field. Bacteria phage DNA molecules Lambda (48.5 kb) and Human BAC clone (170 kb) were stained with the dye YOYO-I. This solution of stained DNA is diluted to 0.5 μg/mL into 0.5×TBE containing 0.1 M dithiothreatol as an anti-oxidant and 0.1% of a linear acrylamide used as an anti-sticking agent.

An Olympus Ix-71 inverted microscope with a 100× (N.A.I.35) oil immersion objective is used with a solid-state laser (e.g., diode pumped solid state laser), which can have different excitation wavelengths (e.g., 473 nm for YOYO-I dye). Other lasers (e.g., for Alexa series of dyes, Cy3, Cy5, etc.) include a 532 nm DPSS laser, a 635 Laser Diode laser, a 543 nm gas laser, a 591 nm DPSS laser, and a 633 nm gas laser. An ANDOR cooled-EMCCD camera with a 512×512 pixel array and 16 bits digital output is used to image the molecules. Digital images are analyzed using a data processor by J-image and other analysis software.

Example 7

Detection Schemes

In one example of a detection scheme, video images of DNA moving in flow mode are captured by a time delay and integration (TDI) camera. In such an embodiment, the movement of the DNA is synchronized with the TDI.

In another example of a detection scheme, video images of a DNA moving in flow mode are capture by a CCD or CMOS camera, and the frames are integrated by software or hardware to indentify and reconstruct the image of the DNA.

In another example of a detection scheme, video images of a DNA are collected by simultaneously capturing different wavelengths on a separate set of sensors. This is accomplished by using one camera and a dual or multi-view splitter, or using by filters and multiple cameras. The camera can be a TDI, CCD or CMOS detection system.

In another example, using simultaneous multiple wavelength video detection, a backbone dye is used to identify a unique DNA fragment, and the labels are used as markers to follow the DNA movement. This is useful in cases where the DNA's length is greater than the field of view of the camera, and the markers can serve to help map a reconstructed image of the DNA.

What is claimed:

1. A method of characterizing a first single-molecule DNA, comprising:
    labeling a plurality of sequence-specific locations on the first single-molecule DNA with a labeling technique that does not comprise labeling a cut or nicked strand of the first single-molecule DNA;
    linearizing at least a portion of the labeled first single-molecule DNA in a nanochannel by physical-entropic confinement of the first single-molecule DNA; and
    detecting a recognizable pattern of label positions on the linearized first single-molecule DNA or portion thereof in the nanochannel, wherein said detecting comprises simultaneously detecting genomic sequence information and epigenomic pattern information in the same field of view on the linearized first single-molecule DNA or portion thereof,
    wherein said detecting comprises detecting at least one of a fluorescent signal, a chemoluminescent signal, an electromagnetic signal, an electrical signal, or a potential difference, and wherein detecting said genomic sequence information comprises detecting a signal, wavelength, or signal and wavelength different from detecting said epigenomic pattern information.

2. The method of claim 1, wherein the recognizable pattern of labels comprises a pattern of one or more selected from the group consisting of: a structure, a sequence assembly, a genetic map, a cytogenetic map, a methylation pattern, a physiological characteristic, a location of a CpG island, an epigenomic pattern, and a combination thereof.

3. The method of claim 1, wherein the first single-molecule DNA is double stranded.

4. The method of claim 1, wherein the labeling is effected with one or more selected from the group consisting of a methyltransferase, a zinc finger protein, an antibody, a transcription factor, a DNA binding protein, a hairpin polyamide, a triplex-forming oligodeoxynucleotide, a peptide nucleic acid, and any combination thereof.

5. The method of claim 1, wherein the labeling is effected with a methyltransferase.

6. The method of claim 1, wherein the label further comprises a fluorophore or quantum dot.

7. The method of claim 1, further comprising labeling at least one additional sequence-specific location on the first single-molecule DNA with a label that differs from the label of claim 1.

8. The method of claim 7, wherein one label identifies genomic information, and wherein the other label identifies epigenomic information.

9. The method of claim 1, wherein the nanochannel has a diameter of about 10 nm to about 200 nm.

10. The method of claim 1, wherein the labeling technique does not comprise hybridization of a sequence-specific nucleic acid probe.

11. A method of characterizing a first single-molecule DNA and a second single-molecule DNA, comprising:
    labeling a plurality of sequence-specific locations on the first single-molecule DNA and the second single-molecule DNA with a labeling technique that does not comprise labeling a cut or nicked strand of either the first single-molecule DNA or the second single-molecule DNA;
    linearizing at least a portion of the labeled first single-molecule DNA and a portion of the labeled second single-molecule DNA in a nanochannel, wherein said linearizing is by physical-entropic confinement of the first single-molecule DNA; and
    detecting a recognizable pattern of label positions on the linearized first single-molecule DNA or portion thereof and on the linearized second single-molecule DNA or portion thereof, wherein said detecting comprises simultaneously detecting genomic sequence information and epigenomic pattern information in a first same field of view on the first single-molecule DNA and simultaneously detecting genomic sequence information and epigenomic pattern information in a second same field of view on the linearized second single-molecule DNA, and
    wherein said detecting comprises detecting at least one of a fluorescent signal, a chemoluminescent signal, an electromagnetic signal, an electrical signal, or a potential difference, and wherein detecting said genomic sequence information comprises detecting a signal, wavelength, or signal and wavelength different from detecting said epigenomic pattern information.

12. The method of claim 11, wherein the first and second single-molecule DNAs are each double stranded.

13. The method of claim 12, wherein the labeling is effected with one or more selected from the group consisting of a methyltransferase, a zinc finger protein, an antibody, a transcription factor, a DNA binding protein, a hairpin polyamide, a triplex-forming oligodeoxynucleotide, a peptide nucleic acid, and a combination thereof.

14. The method of claim 12, wherein the labeling is effected with a methyltransferase.

15. The method of claim 12, wherein the label further comprises a fluorophore or quantum dot.

16. The method of claim 12, further comprising labeling at least one additional sequence-specific location on the first single-molecule DNA with a label that differs from the label of claim 12.

17. The method of claim 16, wherein one label identifies genomic information, and wherein the other label identifies epigenomic information.

18. The method of claim 11, wherein the nanochannel has a diameter of about 10 nm to about 200 nm.

19. The method of claim 11, wherein the labeling technique does not comprise hybridization of a sequence-specific nucleic acid probe.

20. A method of characterizing a single-molecule DNA, comprising:

labeling at least a portion of the single-molecule DNA with a methyltransferase-mediated labeling technique that does not comprise labeling a cut or nicked strand of the DNA;

maintaining at least the portion of the labeled single-molecule DNA in a linearized form in a nanochannel; and simultaneously detecting a plurality of signals in a same field of view from the linearized labeled single-molecule DNA or portion thereof, wherein said detecting comprises simultaneously detecting genomic sequence information and epigenomic pattern information in the same field of view on the labeled single-molecule DNA, wherein said detecting comprises detecting at least one of a fluorescent signal, a chemoluminescent signal, an electromagnetic signal, an electrical signal, or a potential difference, and wherein detecting said genomic sequence information comprises detecting a signal, wavelength, or signal and wavelength different from detecting said epigenomic pattern information.

21. The method of claim 20, wherein the single-molecule DNA is double stranded.

22. The method of claim 21, further comprising:

measuring the intensity of the at least one signal, wherein the at least one signal comprises a signal of one or more selected from the group consisting of: a structure, a sequence assembly, a genetic or cytogenetic map, a methylation pattern, a physiological characteristic, a location of a CpG island, an epigenomic pattern, and a combination thereof.

23. The method of claim 21, further comprising:

detecting a pattern of labels on the labeled double-stranded DNA, wherein the pattern of labels comprises a pattern of one or more selected from the group consisting of: a structure, a sequence assembly, a genetic or cytogenetic map, a methylation pattern, a physiological characteristic, a location of a CpG island, an epigenomic pattern, and a combination thereof.

* * * * *